(12) United States Patent
Vardi

(10) Patent No.: US 8,337,388 B2
(45) Date of Patent: Dec. 25, 2012

(54) SYSTEM AND METHOD TO RESTRICT STOMACH SIZE

(76) Inventor: Gil Vardi, Town and Country, MO (US)

( * ) Notice: Subject to any disclaimer, the term of this patent is extended or adjusted under 35 U.S.C. 154(b) by 1127 days.

(21) Appl. No.: 11/717,254

(22) Filed: Mar. 12, 2007

(65) Prior Publication Data

US 2007/0203511 A1 Aug. 30, 2007

Related U.S. Application Data

(63) Continuation-in-part of application No. 11/257,336, filed on Oct. 24, 2005.

(51) Int. Cl.
*A61B 17/00* (2006.01)
(52) U.S. Cl. .......................... 600/37; 606/157
(58) Field of Classification Search ............ 600/37; 606/139–158; 623/1.1–1.54, 23.7
See application file for complete search history.

(56) References Cited

U.S. PATENT DOCUMENTS

| | | | |
|---|---|---|---|
| 5,320,632 A | 6/1994 | Heidmueller | |
| 5,368,601 A | 11/1994 | Sauer et al. | |
| 5,397,355 A * | 3/1995 | Marin et al. | 623/1.2 |
| 5,800,526 A * | 9/1998 | Anderson et al. | 623/1.16 |
| 5,865,791 A | 2/1999 | Whayne et al. | |
| 6,036,699 A | 3/2000 | Andreas et al. | |
| 6,113,609 A | 9/2000 | Adams | |
| 6,517,573 B1 * | 2/2003 | Pollock et al. | 623/1.15 |
| 6,547,801 B1 | 4/2003 | Dargent et al. | |
| 6,558,400 B2 | 5/2003 | Deem et al. | |
| 6,572,627 B2 | 6/2003 | Gabbay | |
| 6,602,263 B1 * | 8/2003 | Swanson et al. | 606/153 |
| 6,746,460 B2 | 6/2004 | Gannoe et al. | |
| 6,755,869 B2 | 6/2004 | Geitz | |
| 6,802,868 B2 | 10/2004 | Silverman et al. | |
| 7,033,384 B2 | 4/2006 | Gannoe et al. | |
| 7,037,344 B2 | 5/2006 | Kagan et al. | |
| 7,090,699 B2 | 8/2006 | Geitz | |
| 7,211,094 B2 | 5/2007 | Gannoe et al. | |
| 7,708,684 B2 * | 5/2010 | Demarais et al. | 600/37 |
| 2003/0093117 A1 | 5/2003 | Saadat | |
| 2004/0092892 A1 * | 5/2004 | Kagan et al. | 604/264 |
| 2004/0122456 A1 | 6/2004 | Saadat et al. | |
| 2004/0148034 A1 | 7/2004 | Kagan et al. | |
| 2005/0096750 A1 | 5/2005 | Kagan et al. | |
| 2006/0036267 A1 | 2/2006 | Saadat et al. | |
| 2010/0312323 A1 * | 12/2010 | Majercak et al. | 623/1.11 |

* cited by examiner

*Primary Examiner* — Charles A Marmor, II
*Assistant Examiner* — Catherine E Burk
(74) *Attorney, Agent, or Firm* — Armstrong Teasdale LLP

(57) ABSTRACT

A device for restricting a cross-sectional area of a cavity formed by a stomach wall includes a band defining a cylindrical wall and a plurality of retaining members formed within the wall. Each retaining member is movable between a retracted position substantially coplanar with an outer surface of the wall and an extended position extending radially outwardly from the wall to facilitate coupling the device to the stomach wall.

15 Claims, 17 Drawing Sheets

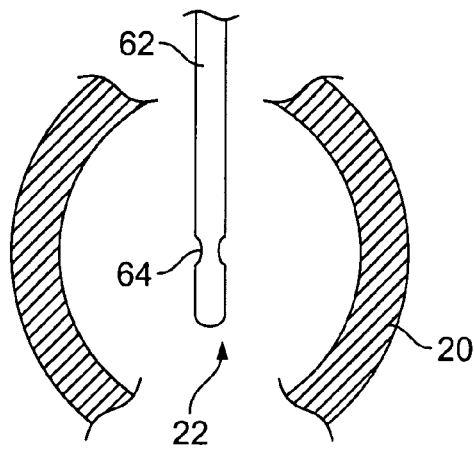 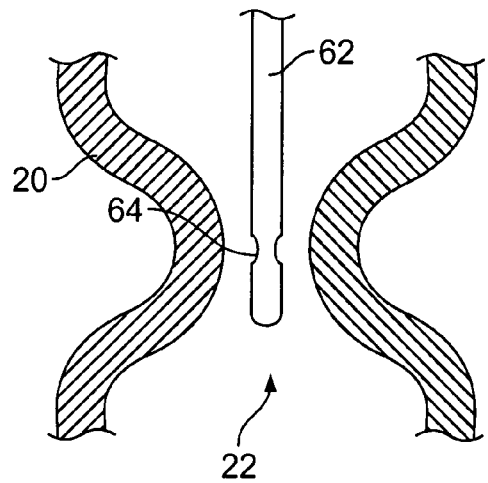
FIG. 10  FIG. 11
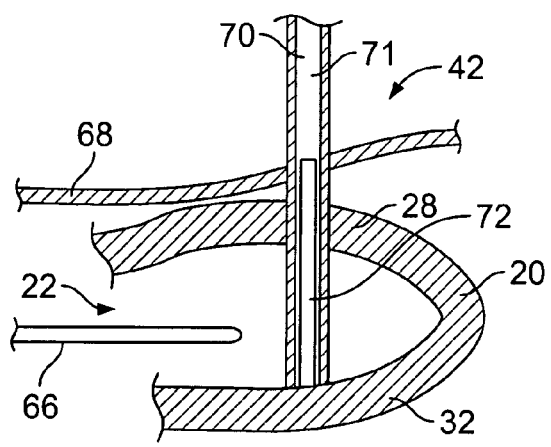 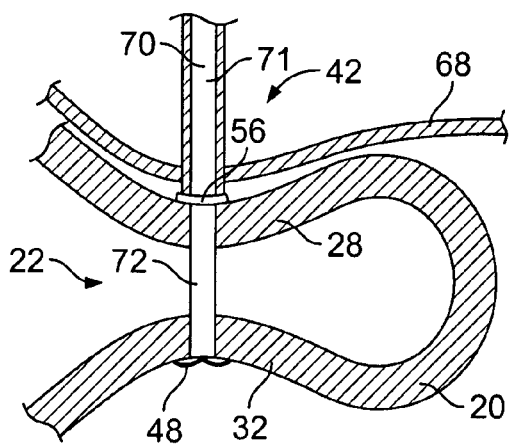
FIG. 12  FIG. 13

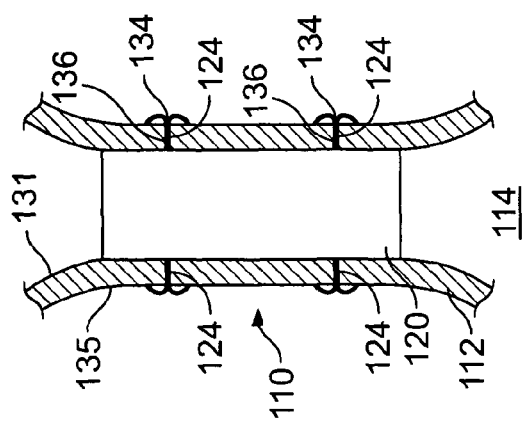
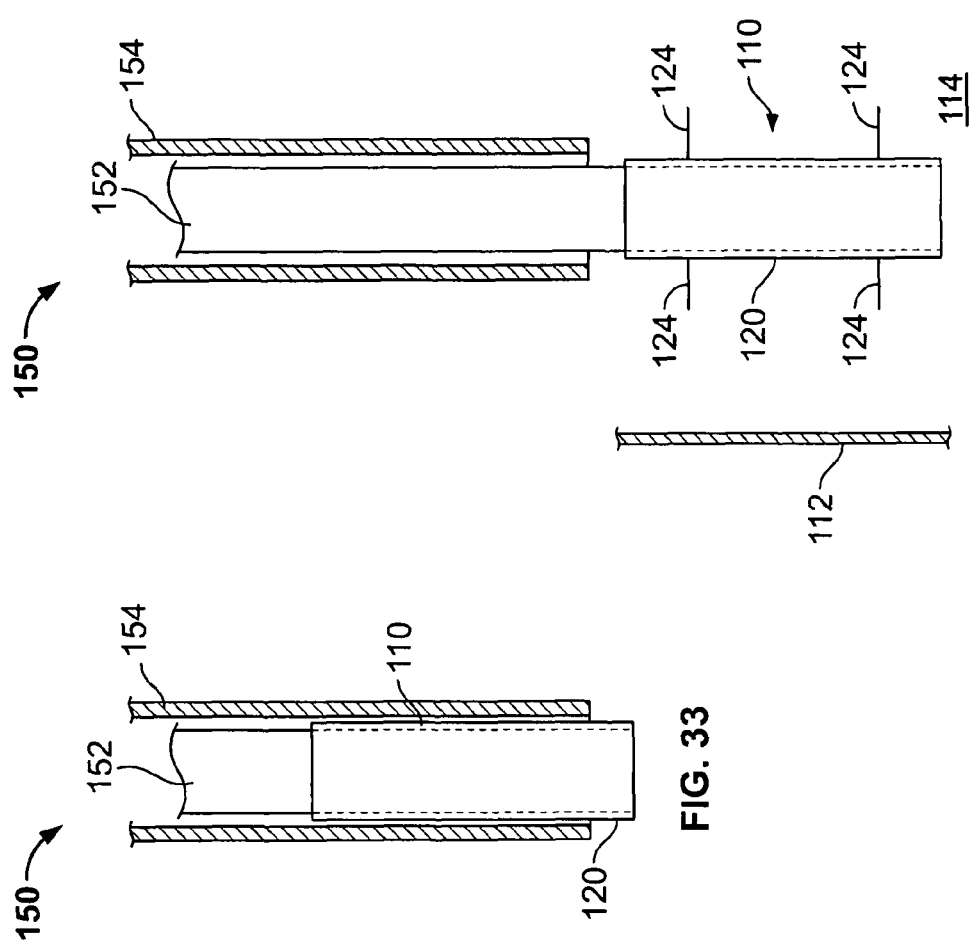

SYSTEM AND METHOD TO RESTRICT STOMACH SIZE

CROSS REFERENCE TO RELATED APPLICATIONS

This is a continuation-in-part application of application Ser. No. 11/257,336, filed on Oct. 24, 2005, which is hereby incorporated by reference in its entirety.

BACKGROUND OF THE INVENTION

This invention relates generally to gastric reduction and, more particularly, to a system and method for restricting a cross-sectional area of a cavity formed by a stomach wall.

Morbid obesity is a major health concern in the United States and other countries. Morbid obesity commonly results in advancement of diseases and conditions, such as heart disease, hypertension, diabetes, heart failure and other related health complications.

Many treatments and surgical procedures have been developed for patients whose health and quality of life have suffered as a result of being morbidly obese. Conventional surgical procedures typically involve invasive procedures to permanently decrease the volume of the patient's stomach or bypass a portion of the stomach and/or small intestine.

BRIEF DESCRIPTION OF THE INVENTION

In one aspect, a device is provided for restricting a cross-sectional area of a cavity formed by a stomach wall. The device includes a band defining a cylindrical wall and a plurality of retaining members formed within the wall. Each of the plurality of retaining members is movable between a retracted position substantially coplanar with an outer surface of the wall and an extended position extending radially outwardly from the wall to facilitate coupling the device to the stomach wall.

In another aspect, a system is provided for restricting a cross-sectional area of a cavity formed by a stomach wall. The system includes a catheter. A device is initially positioned about the catheter that includes a band defining a cylindrical wall and a plurality of retaining members formed within the wall. Each of the plurality of retaining members is movable between a retracted position and an extended position. In the extended position, each retaining member extends radially outwardly from the wall to facilitate coupling the device to the stomach wall. A sheath is movably positioned about the band to facilitate retaining each retaining member in the retracted position.

In another aspect, a method is provided for restricting a cross-sectional area of a cavity formed by a stomach wall. The method includes introducing into the cavity a device configured to restrict the cross-sectional area of the cavity. The device includes a band defining a cylindrical wall and a plurality of retaining members formed within the wall. Each of the plurality of retaining members is movable between a retracted position substantially coplanar with an outer surface of the wall and an extended position extending radially outwardly from the wall to facilitate coupling the device to the stomach wall. The stomach wall is collapsed to urge the stomach wall towards the device. The device is coupled to the stomach wall to secure the cavity in a restricted configuration.

BRIEF DESCRIPTION OF THE DRAWINGS

FIG. 10 is a sectional view of a stomach and a device for restricting a cross-sectional area of a cavity formed by the stomach, according to one embodiment of the invention.

FIG. 11 shows the device of FIG. 10 with the stomach wall in a restricted position.

FIG. 12 is a partial sectional view of a patient's body and a device percutaneously inserted into the patient's stomach for restricting a cross-sectional area of a cavity formed by the stomach, according to one embodiment of the invention.

FIG. 13 shows the device of FIG. 12 with the stomach wall in a restricted position.

FIG. 33 is a partial sectional view of an exemplary system for restricting a cross-sectional area of a cavity defined by a stomach wall.

FIG. 34 is a partial sectional view of the system shown in FIG. 23 with a sheath retracted from about a device.

FIG. 35 is a partial sectional view of the system shown in FIG. 24 with the device coupled to the stomach wall to restrict a cross-sectional area of the stomach cavity.

DETAILED DESCRIPTION OF THE INVENTION

Referring to FIGS. 1-35, the present invention is directed to a device and a system for closing or constricting an opening formed by a stomach wall, for example by restricting a cross-sectional area of a cavity formed by the stomach wall. Although the following description relates to constricting an opening formed by the stomach wall, the device and system of the present invention may be suitable for constricting other openings or orifices formed by or in a patient's body, as well as for connecting or attaching tissue and other body parts, for example.

Figure 1:
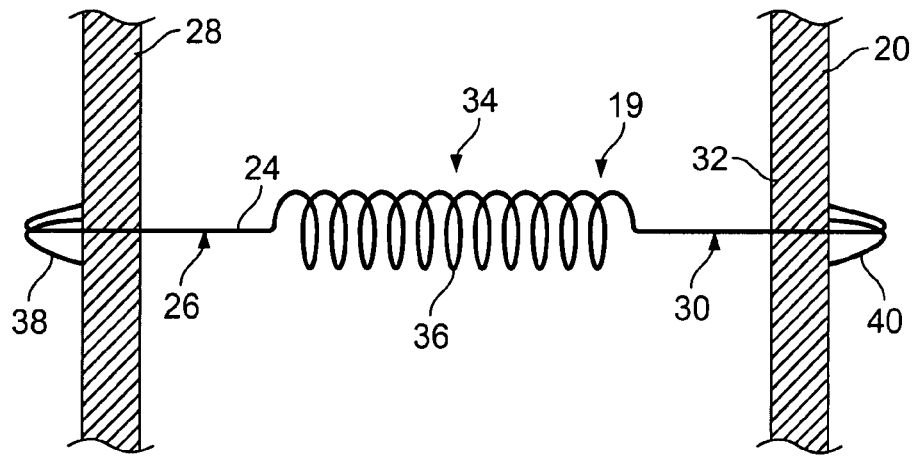
FIG. 1 is a partial sectional view of a stomach with a device for restricting a cross-sectional area of a cavity formed by the stomach attached to opposing portions of the stomach wall, according to one embodiment of the invention.

In one embodiment, an implantable device 19 for gastric reduction is shown in FIG. 1. Device 19 can be used to constrict an opening formed by a stomach wall 20, such as to restrict a cross-sectional area of a cavity 22 formed by the stomach wall. Device 19 includes a restricting and/or supporting member 24 having a first end 26 connectable or attachable to a first portion of the stomach wall, such as an anterior portion 28 of the stomach wall, and an opposing second end 30 connectable or attachable to a second portion of the stomach wall, such as a posterior portion 32 of the stomach wall. In one embodiment, first end 26 and second end 30 are attached or connected to generally opposing portions of the stomach wall. Alternatively, second end 30 may be generally radially offset with respect to first end 26 along an inner surface of the stomach wall forming the cavity.

Member 24 is preferably made of a biocompatible material including, without limitation, suitable metal materials, such as stainless steel, platinum, gold, titanium and nickel and/or composites or alloys thereof. In one embodiment, member 24 has shape memory properties and is adapted to move first end 26 towards second end 30. For example, in one embodiment, member 24 is made or fabricated from Nitinol. Nitinol possesses shape memory properties that allow the material to return to an initial configuration after a force applied to the material to shape, stretch, compress and/or deform the material is removed. It should be apparent to those having ordinary skill in the art and guided by the teachings herein provided that member 24 may be made or fabricated using any suitable biocompatible materials, including suitable polymeric materials, such as polyurethane materials, preferably having suitable shape memory properties.

Member 24 may have any suitable size, shape and/or configuration, which provide sufficient structural strength required by the present invention. For example, in one embodiment, device 19 includes at least one member 24 shaped as a wire, tube or cylinder, as shown in FIG. 1. The wire, tube or cylinder has a generally circular cross-sectional area. Alternatively, or in addition, device 19 may include at least one member 24 having a generally rectangular cross-sectional area or any other suitable polygonal cross-sectional area.

As shown in FIG. 1, member 24 includes a body 34 extending between first end 14 and second end 16. In one embodiment, body 34 includes a biasing element 36, such as a spring or a coil, which exerts a biasing force, such as a tension force. With member 24 in a deployed configuration, in which first end 26 is secured to anterior portion 28 and second end 30 is secured to posterior portion 32 for example, biasing element 36 exerts a tension force at first end 26 and/or second end 30 sufficient to urge first end 26 towards second end 30 and, thus, urge anterior portion 28 of the stomach wall towards posterior portion 32 of the stomach wall to restrict the cross-sectional area of stomach cavity 22, as desired. In one embodiment, biasing element 36 is generally positioned at a mid-section of member 24 and provides a generally equal amount of force to first end 26 and second end 30. In alternate embodiments, biasing element 36 may be positioned on member 24 at a suitable location to provide a desired or selected force to first end 26 and/or second end 30.

In one embodiment, a first fastener 38 or other suitable connector connects or attaches first end 26 to the first portion of the stomach wall. Similarly, a second fastener 40, preferably the same or similar to first fastener 38, connects or attaches second end 30 to the second portion of the stomach wall. Each fastener 38, 40 is integrated with respective end 26, 30. Alternatively, fasteners 38, 40 are independent components attached or connected to member 24 using a suitable connector.

Fasteners 38, 40 may include any suitable attachment component to assist in attaching and/or securing fasteners 38, 40 with respect to the stomach wall. For example, fasteners 38, 40 include at least one flexible needle or hook each having a tip portion that extends through the stomach wall and is secured to an outer surface of the stomach wall, as shown in FIG. 1. In one embodiment, each fastener 38, 40 includes a plurality of hooks that are shapeable or bendable. Upon penetrating a thickness of the stomach wall, each hook extends radially outwardly to contact and/or interfere with an outer surface of the stomach wall and secure the respective end 26, 30 of member 24 with respect to the stomach wall. Alternatively, or in addition, fasteners 38, 40 may include a suture, staple or a suitable mechanical component that penetrates at least an inner surface of the stomach wall and extends at least partially through the stomach wall thickness.

In an alternative embodiment, implantable device 19 includes at least one magnet positioned with respect to each end 26, 30 of member 24. For example, a magnet is positioned at first end 26 and opposing second end 30 to magnetically urge first end 26 towards second end 30 and, thus, magnetically urge anterior portion 28 of the stomach wall towards posterior portion 32 of the stomach wall to restrict the cross-sectional area of stomach cavity 22, as desired. Alternatively, or in addition, each fastener 38, 40 includes a magnetic component that urges anterior portion 28 towards posterior portion 32 to restrict the cross-sectional area of stomach cavity 22, as desired.

Figure 2:
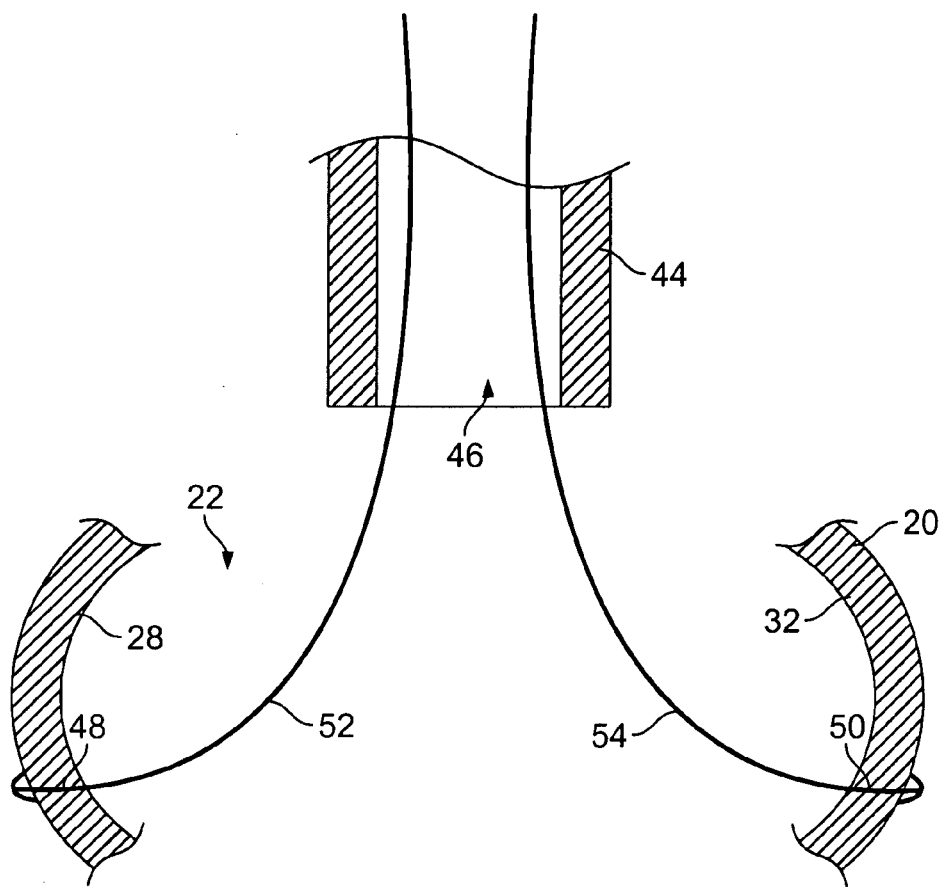
FIG. 2 is a partial sectional view of a stomach and a system for restricting a cross-sectional area of a cavity formed by the stomach, according to one embodiment of the invention.
Figure 3:
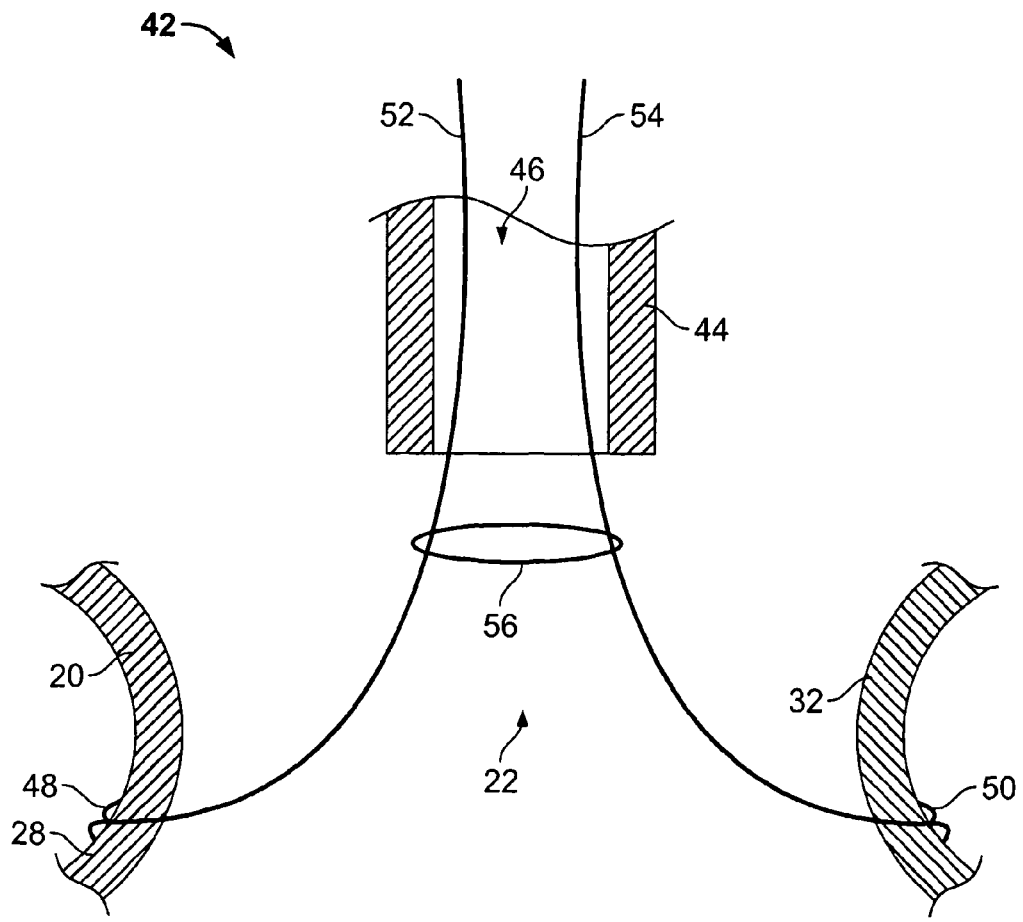
FIG. 3 shows the system of FIG. 2 with the stomach wall in a restricted position.

A system 42 for gastric reduction according to one embodiment is shown in FIGS. 2 and 3. System 42 is used to constrict an opening formed by stomach wall 20, such as to restrict a cross-sectional area of cavity 22 formed by the stomach wall. System 42 includes a catheter 44 forming a passage 46. In one embodiment, catheter 44 includes any suitable catheter component known to those skilled in the art and is introduced into a patient's body using any suitable or desirable method. For example, catheter 44 is directed through the patient's mouth and esophagus and into an opening formed by the stomach wall. Alternatively, as discussed in greater detail below, a catheter is introduced into the patient's stomach cavity percutaneously, e.g., by insertion through the patient's skin.

As shown in FIGS. 2 and 3, system 42 includes a first fastener 48 and an independent second fastener 50. Fasteners 48, 50 are at least partially positioned initially within passage 46 in a retracted configuration, to assist in the insertion of system 42 into the patient's body and stomach cavity. Upon introduction into the stomach cavity, each fastener 48, 50 is extended to connect to a portion of the stomach wall and movable to a deployed configuration to secure the fastener to the stomach wall. Preferably, fasteners 48, 50 are independently movable between the retracted configuration and the deployed configuration.

In one embodiment, fasteners 48, 50 are translatable with respect to catheter 44. Fastener 48 is movable from within passage 46 and attachable or connectable to a first portion of the stomach wall, such as anterior portion 28. Preferably, fastener 48 is connected or attached to a proximal end of a member 52 that is initially positioned within passage 46. Member 52 is preferably a suture or a wire that extends through passage 46 and is translatable with respect to catheter 44 along a length of passage 46.

Upon attachment to the first portion, fastener 48 is movable to the deployed configuration to secure attachment of fastener 48 to the first portion. Preferably, fastener 48 extends into and at least partially through a thickness of the stomach wall at the first portion. For example, as shown in FIG. 3, fastener 48 extends through the stomach wall and contacts an outer surface of the stomach wall to secure fastener 48 with respect to the first portion of the stomach wall. Fastener 48 may include any suitable attachment component to assist in attaching fastener 48 with respect to the first portion of the stomach wall. For example, fastener 48 includes at least one flexible needle or hook having a tip portion that extends or passes through the stomach wall and is secured to the outer surface of the stomach wall at the first portion. Alternatively, or in addition, fastener 48 includes a suture, a staple or other suitable mechanical component that penetrates at least an inner surface of the stomach wall. In an alternative embodiment, a magnet or a magnetic component is positioned with respect to each fastener 38, 40 to magnetically urge the first portion of the stomach wall towards the second portion of the stomach wall to restrict the cross-sectional area of stomach cavity 22, as desired.

Similarly, fastener 50 is movable from within passage 46 and attaches to a second portion of the stomach wall, such as posterior portion 32. Fastener 50 is preferably connected at a position on the inner surface of the stomach wall radially offset with respect to the position on the inner surface at which fastener 48 is attached to the stomach wall. In one embodiment, fastener 50 is attached to the stomach wall generally opposing fastener 48. Fastener 50 is at least partially positioned within passage 46 in an initial or retracted configuration for insertion into the stomach cavity. Within the stomach cavity, fastener 50 is extendable to a second portion of the stomach wall opposing the first portion of the stomach wall to which fastener 48 is connected.

In one embodiment, fastener 50 is connected to a proximal end of a member 54 that is initially positioned within passage 46. Member 54 is preferably a suture or wire that extends through passage 46 and is translatable with respect to catheter 44, independently of member 52, along a length of passage 46.

Figures 4, 5:
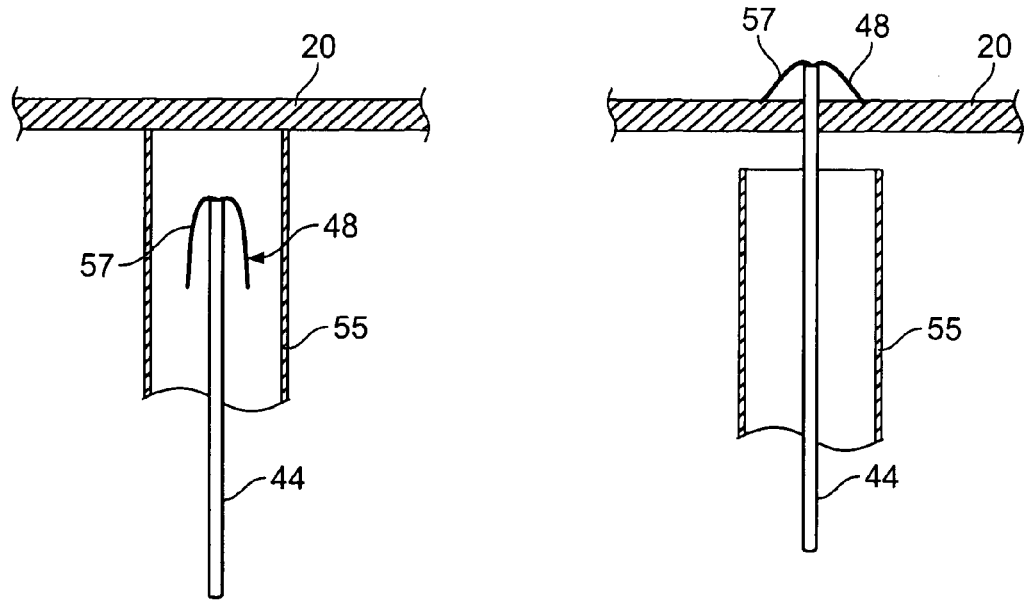
FIG. 4 is a partial sectional view of a stomach wall and a fastener initially positioned within a sheath, according to one embodiment of the invention.
FIG. 5 shows the fastener of FIG. 4 in a deployed position and contacting the outer surface of the stomach wall.

In one embodiment, each fastener 48, 50 includes at least one flexible needle or hook that punctures and penetrates the stomach wall to contact the outer surface of the stomach wall and maintain a secure connection thereto. In the deployed configuration, each fastener 48, 50 is configured to curve or bend, for example as a result of the shape memory of the material used to fabricate the fasteners, to maintain each fastener 48, 50 securely positioned with respect to the stomach wall. In one embodiment, each fastener 48, 50 is initially positioned within a sheath 55 that maintains flexible hooks 57 of fasteners 48, 50 in the retracted position, as shown in FIG. 4. After fasteners 48, 50 penetrate the stomach wall, sheath 55 is movable along respective member 52, 54 to expose hooks 57. Each hook 57 moves to the deployed position, as a result of material shape memory for example, to contact the outer surface of the stomach wall and maintain a secure connection thereto, as shown in FIG. 5.

Figure 6:
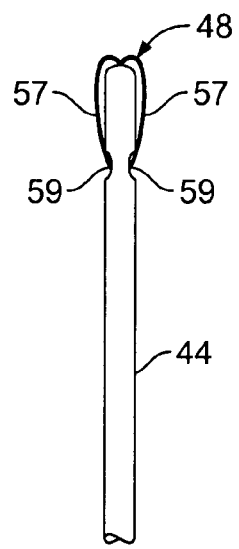
FIG. 6 shows a fastener initially positioned within a groove formed in a catheter, according to one embodiment of the invention.
Figure 7:
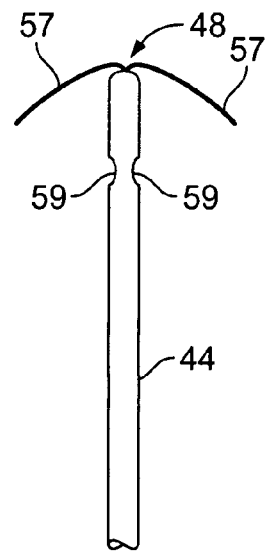
FIG. 7 shows the fastener of FIG. 6 in a deployed position.

In an alternative embodiment, each fastener 48, 50 is initially retained within a groove 59 formed in catheter 44, as shown in FIG. 6. After fasteners 48, 50 penetrate the stomach wall, hooks 57 are released from within groove 59 by a twisting motion of catheter 44. Each hook 57 moves to the deployed position to contact the outer surface of the stomach wall and maintain a secure connection thereto, as shown in FIG. 7. In alternative embodiments, any suitable retainer is used to retain hooks 57 within groove 59 with fasteners 48, 50 in the retracted position. Further, any suitable means known to those skilled in the art and guided by the teachings herein provided may be used to release hooks 57 from the retracted position, as desired.

With fasteners 48, 50 secured with respect to the stomach wall, catheter 44 is movable within the stomach cavity to urge fastener 48 toward fastener 50. For example, catheter 44 is movable along a length of each member 52, 54 to move fasteners 48, 50 together and, thus, urge the first portion of the stomach wall into proximity with the second portion of the stomach wall to close or restrict the cross-sectional area of the stomach cavity. Alternatively, members 52, 54 are pulled together with respect to catheter 44 to move fasteners 48, 50 together.

With fasteners 48, 50 moved together as desired, a retainer 56, such as a ring, a clip, a clamp, a collar or a suitable mechanical connector, is positioned with respect to fasteners 48, 50 to secure the first stomach wall portion in proximity with the second stomach wall portion and, thus, maintain the cross-sectional area of the stomach cavity in a restricted position, as shown in FIG. 3. In the restricted position, the patient is able control food intake, while satisfying his or her appetite and adhering to a dietary plan for losing weight and/or maintaining a healthy weight.

Figure 8:
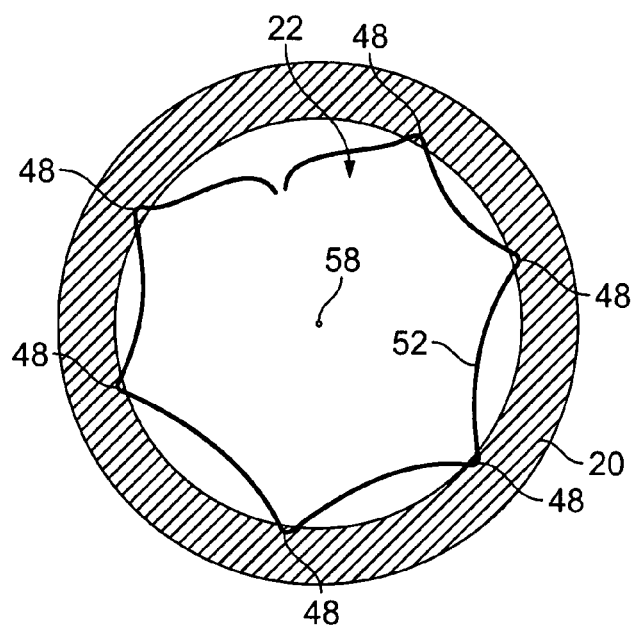
FIG. 8 is a sectional view of a stomach and a device for restricting a cross-sectional area of a cavity formed by the stomach, according to one embodiment of the invention.
Figure 9:
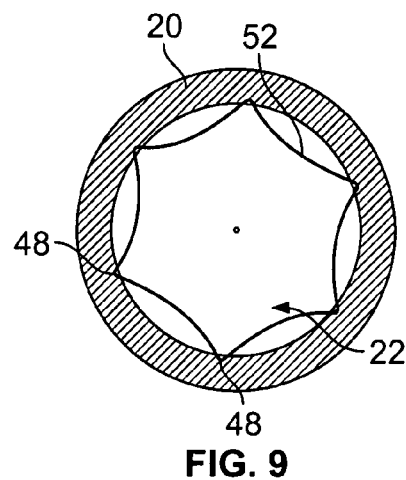
FIG. 9 shows the device of FIG. 8 with the stomach wall in a restricted position.
Figure 16:
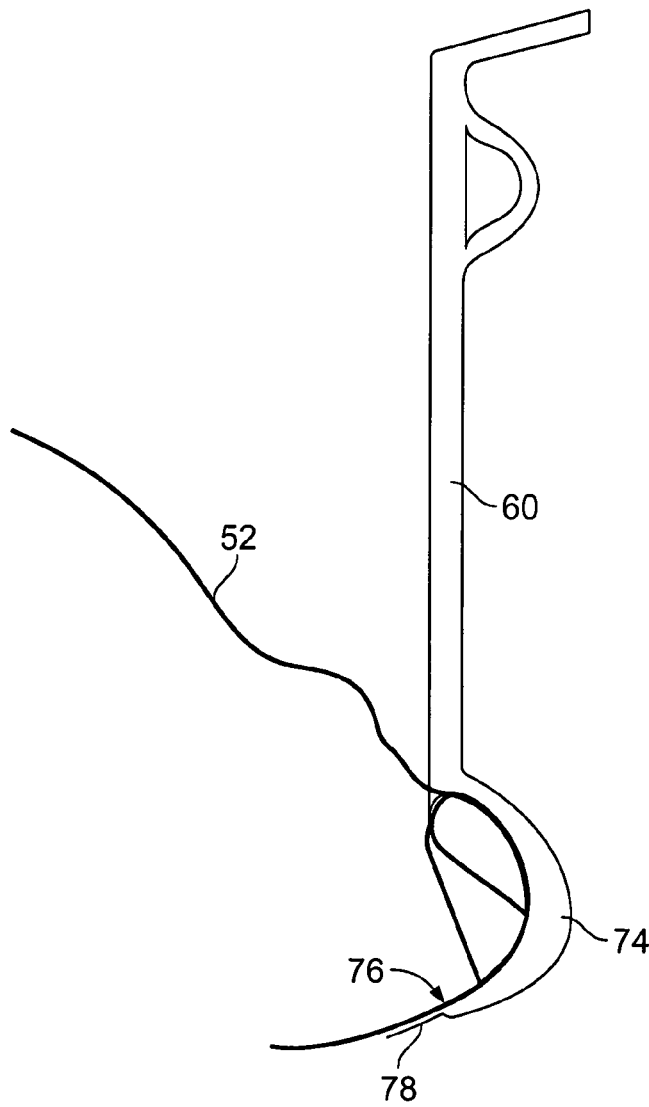
FIG. 16 is a front view of an instrument, according to one embodiment of the invention.

It is apparent to those skilled in the art that the system of the present invention may include any suitable number of fasteners. For example, as shown in FIGS. 8 and 9, in one embodiment, the system includes a plurality of fasteners 48 spaced about the inner surface of the stomach cavity and connected by member 52. By applying a pulling force to member 52, each fastener 48 is drawn or pulled toward a general center point 58 of cavity 22 to restrict the cross-sectional area of the stomach cavity, as shown in FIG. 9. A suitable mechanism or tool, such as a ratcheting tool or a wheel, not shown, may be used to pull member 52 so that fasteners 48 converge to decrease or restrict the cross-sectional area of the stomach cavity. Alternatively, a tool or instrument, such as instrument 60 shown in FIG. 16, is used to suture member 52 about the inner surface of the stomach wall with or without the use of fasteners.

In an alternate embodiment, the cross-sectional area of the stomach cavity is restricted by applying a suction force to constrict the stomach wall. For example, a suitable suction device 62, preferably having a plurality of apertures 64 to provide a suitable or desired suction force, is positioned within cavity 22, as shown in FIGS. 10 and 11. Upon applying a suction force to the stomach wall, portions of the stomach wall are drawn inwardly and the cross-sectional area of stomach cavity 22 is restricted, as shown in FIG. 11. With the suction force applied, member 24 and/or fasteners 48, 50, for example, are connected to the stomach wall to maintain the stomach wall in the restricted position. Alternatively, or in addition, the drawn-in portion of the stomach wall is sutured, wired or stapled, for example, to maintain the stomach wall in the restricted position.

As briefly discussed above, in an alternate embodiment, system 42 is introduced into the patient's stomach cavity percutaneously, to restrict the size of a patient's stomach and/or constrict an opening formed by the stomach wall. Preferably, system 42 is introduced into the stomach cavity with the assistance or guidance of an endoscope 66. Endoscope 66 is inserted into the stomach cavity through the patient's esophagus. A light emitted from endoscope 66 is visible through the skin to allow the doctor to see the impression of the percutaneously-introduced catheter 44 on the stomach wall.

FIGS. 12 and 13 show a device percutaneously inserted into a patient's stomach for restricting a cross-sectional area of a cavity formed by the stomach. In this embodiment, catheter 70 penetrates a patient's skin 68 and a first portion of the stomach wall, preferably anterior portion 28. Catheter 70 proceeds through stomach cavity 22 and penetrates an opposing second portion of the stomach wall, preferably posterior portion 32. As shown in FIG. 13, a catheter passage 71 accepts a fastener 48 during introduction of system 42 into the stomach cavity. Upon insertion of catheter 70 into the stomach cavity, fastener 48 punctures and penetrates at least an inner surface of the stomach wall and is connected to posterior portion 32.

Fastener 48 preferably includes a plurality of shapeable needles or hooks that extend through the thickness of posterior portion 32 and contact the outer surface of the stomach wall at posterior portion 32. A rod 72 is slidably positioned within passage 71 and connected to fastener 48. With fastener 48 secured to posterior portion 32, a retainer 56, such as a clip, a clamp, a collar or a ring, is positioned about an outer periphery of rod 72 and is slidably movable along a length of rod 72 to move anterior portion 28 towards posterior portion 32 and restrict cavity 22. With anterior portion 28 positioned relative to posterior portion 32, retainer 56 maintains rod 72 in position. Alternatively, a fastener, such as fastener 50, attaches rod 72 to anterior portion 28. In one embodiment, an excess or unused portion of rod 72 is detached and removed from the patient's body, along with catheter 70, to complete the procedure.

Figure 14:
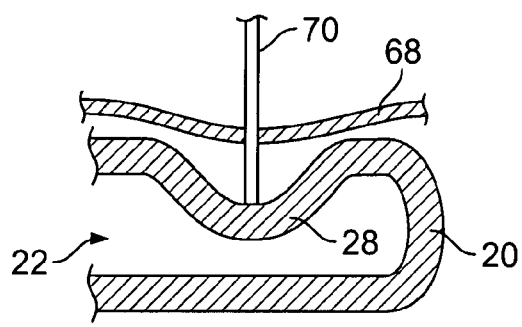
FIG. 14 is a partial sectional view of a patient's body and a device percutaneously inserted into the patient's body for restricting a cross-sectional area of a cavity formed by the stomach wall, according to one embodiment of the invention.
Figure 15:
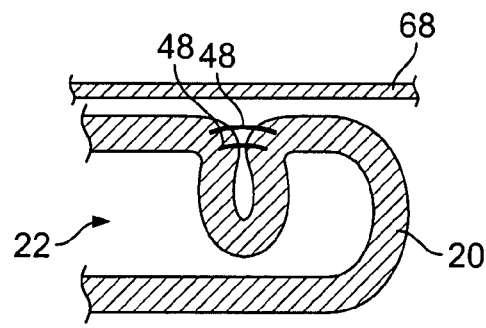
FIG. 15 shows the device of FIG. 14 with the stomach wall in a restricted position.

In an alternate embodiment, system 42 is introduced percutaneously without entering into the patient's stomach cavity to restrict the size of a patient's stomach. Referring to FIGS. 14 and 15, catheter 70 penetrates a patient's skin 68. A suitable force is applied to catheter 70 to depress a portion of the stomach wall, such as anterior portion 28, without puncturing and/or otherwise damaging the outer surface of the stomach wall. As anterior portion 28 is depressed, adjacent portions of the stomach wall converge about catheter 70. The adjacent portions of the stomach wall are connected using a suitable fastener 48, such as a plurality of hooks, staples and/or sutures to restrict the stomach cavity size. Catheter 70 is removed from the patient's body to complete the procedure.

As shown in FIG. 16, surgical instrument 60 is used with device 19 and/or system 42 of the present invention. Instrument 60 includes a distal end portion 74 preferably having an arcuate or semi-circular shape that forms a channel 76 extending at least partially along a length of distal end portion 74. Member 52, or any suitable suturing piece, is positioned within channel 76 and movable within channel 76 with respect to distal end portion 74. A shapeable needle 78 is movably positioned at distal end portion 74 and within channel 76 to allow needle 78 to move in a reciprocating motion with respect to distal end portion 74. As needle 78 reciprocates, needle 78 enters and exits the stomach wall to form a hole therethrough while feeding member 52 through the formed hole. In one embodiment, instrument 60 is utilized to form a plurality of holes about the inner surface of the stomach wall and feed member 52 through the formed holes. Member 52 is then drawn or pulled to converge portions of the stomach wall and restrict a cross-sectional area of the cavity formed by the stomach wall.

Figure 17:
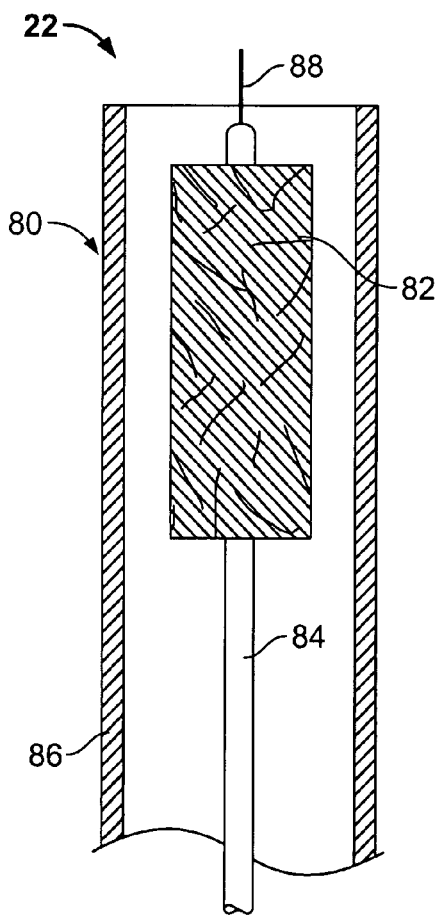
FIG. 17 is a partial sectional view of a device for restricting a cross-sectional area of a cavity formed by the stomach, according to one embodiment of the invention.
Figure 18:
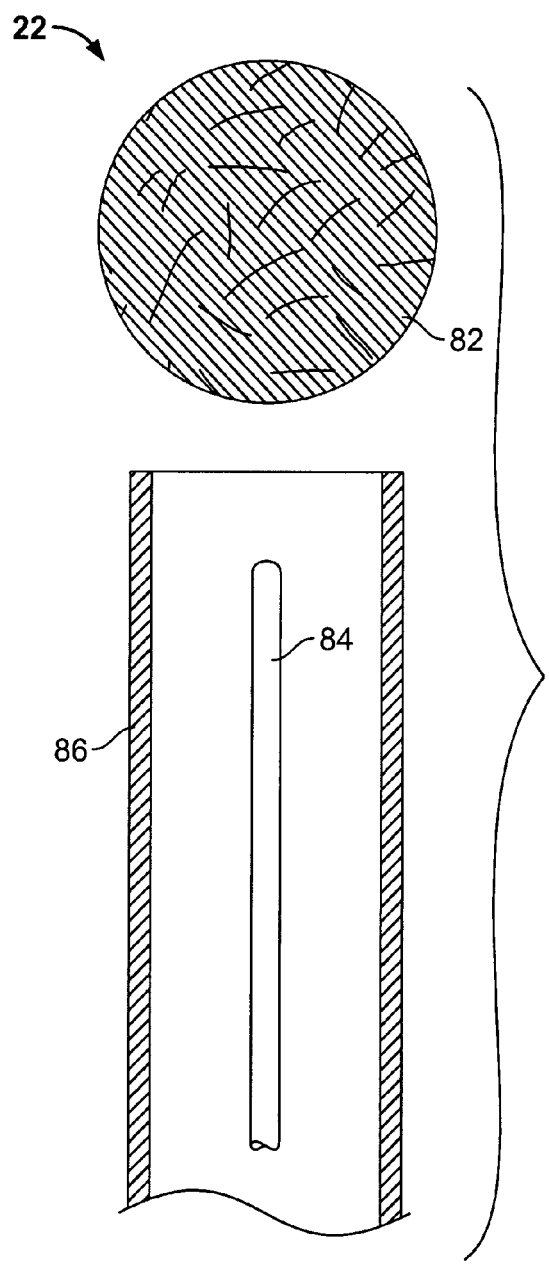
FIG. 18 shows the device of FIG. 17 in an expanded configuration.

FIGS. 17 and 18 show a device 80 that is inserted into a patient's stomach for restricting a cross-sectional area of a cavity formed by the stomach. In one embodiment, device 80 includes an expandable member 82 that is initially positioned in a collapsed position about or within a catheter 84, as shown in FIG. 17. A sheath 86 is positioned about member 80 and at least a portion of catheter 84. In the collapsed position, device 80 is directed into the patient's stomach cavity 22. In one particular embodiment, device 80 is directed into cavity 22 using a suitable guide wire 88. Upon introduction of device 80 into cavity 22, sheath 86 is movable along a length of catheter 84 to expose member 82. Within cavity 22, member 82 expands, as shown in FIG. 18, to restrict a cross-sectional area of cavity 22. In one embodiment, a balloon is used to expand member 82. Member 82 increases in volume to expand to a generally spherical shape having a hollow interior. In alternative embodiments, member 82 has a generally solid interior in the expanded configuration. Further, in alternative embodiments, member 82 has any suitable expanded shape.

In this embodiment, member 82 is fabricated using a Nitinol skeleton including a covering cloth. In alternative embodiments, member 82 includes the skeleton without the covering cloth. Further, member 82 may be fabricated using a suitable biocompatible material known to those skilled in the art and guided by the teachings herein provided.

Figure 19:
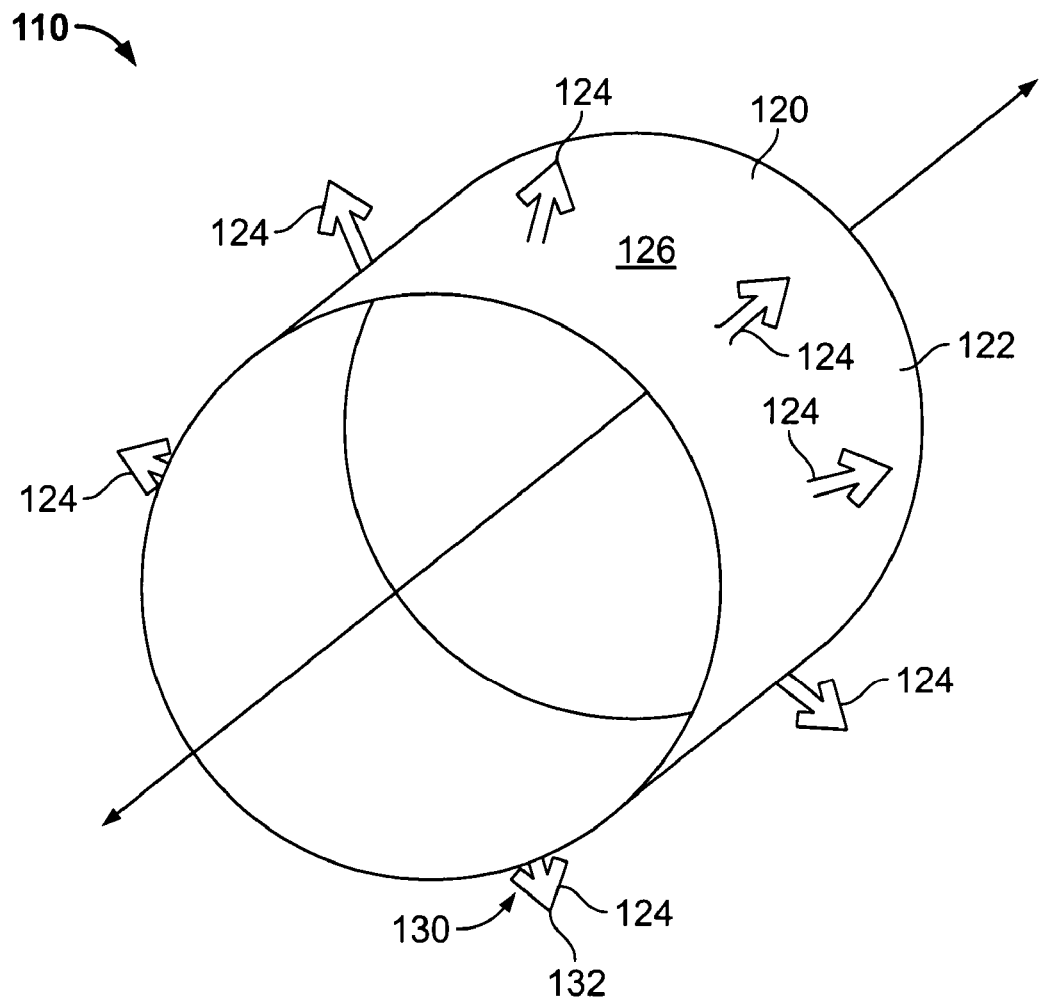
FIG. 19 is a perspective schematic view of an exemplary device for restricting a cross-sectional area of a cavity formed by a stomach wall.
Figure 25:
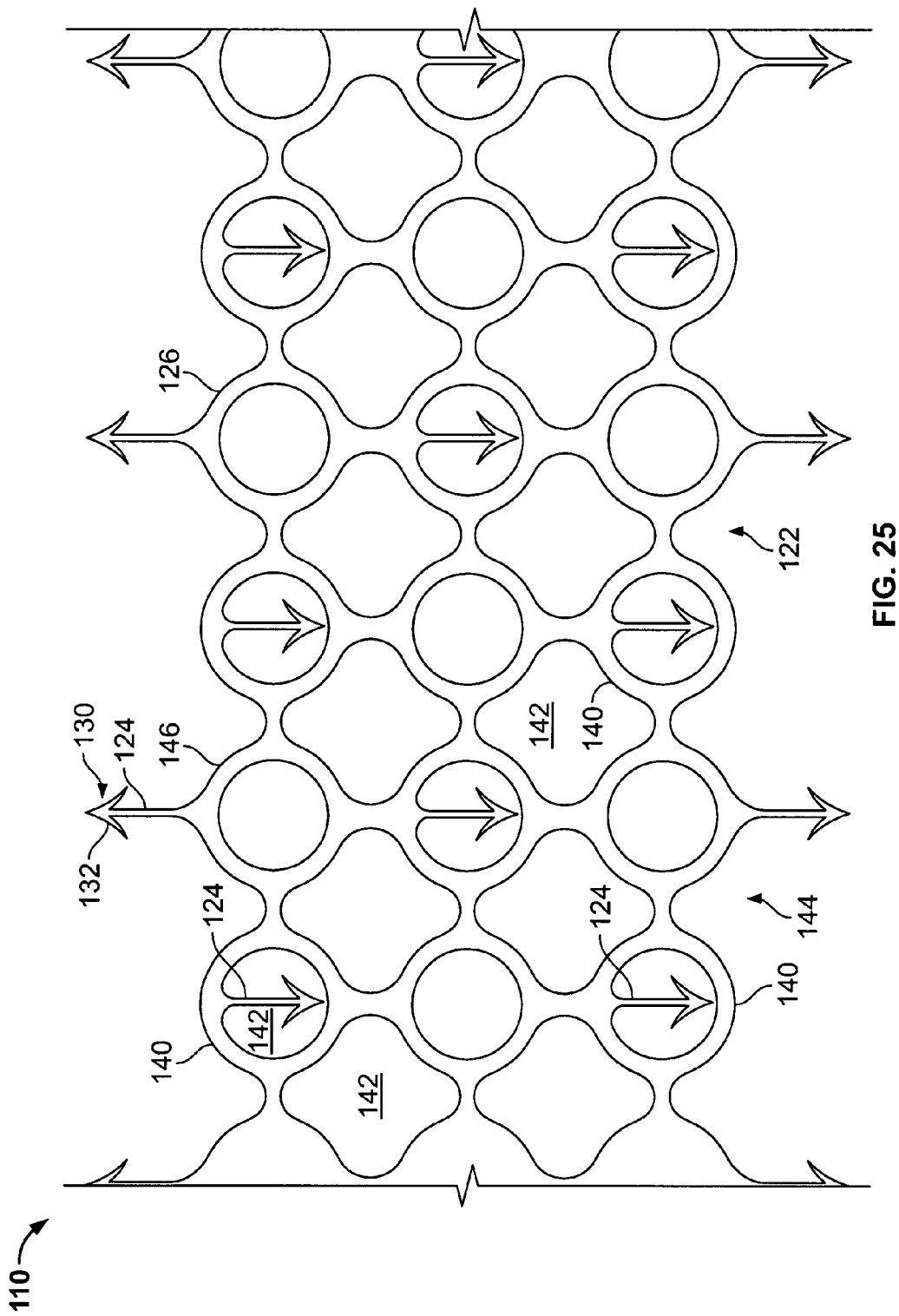
FIG. 25 is a front view of a portion of an alternative exemplary device including a plurality of cells defining a plurality of voids.
Figure 26:
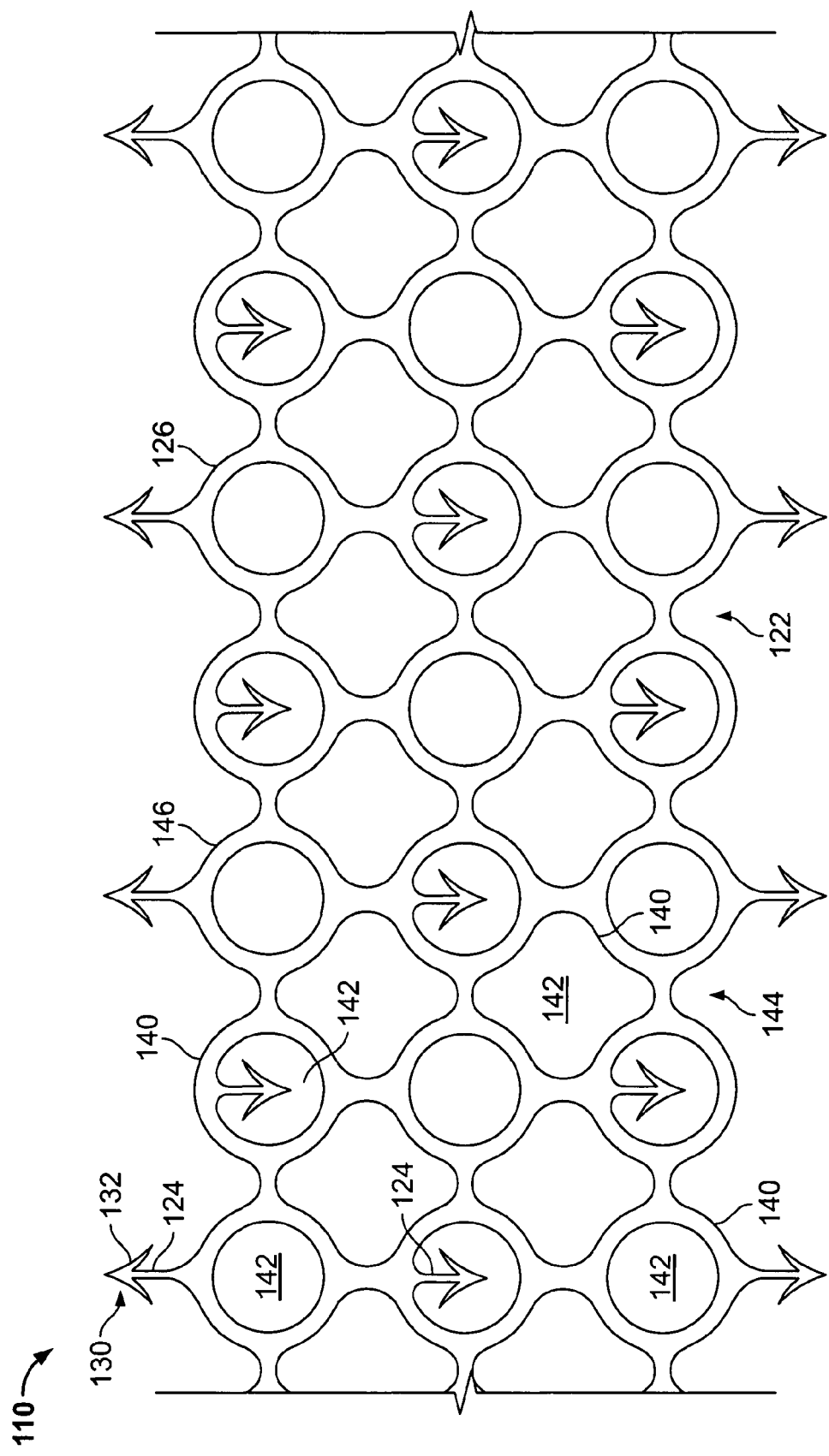
FIG. 26 is a front view of a portion of an alternative exemplary device including a plurality of cells defining a plurality of voids.
Figure 27:
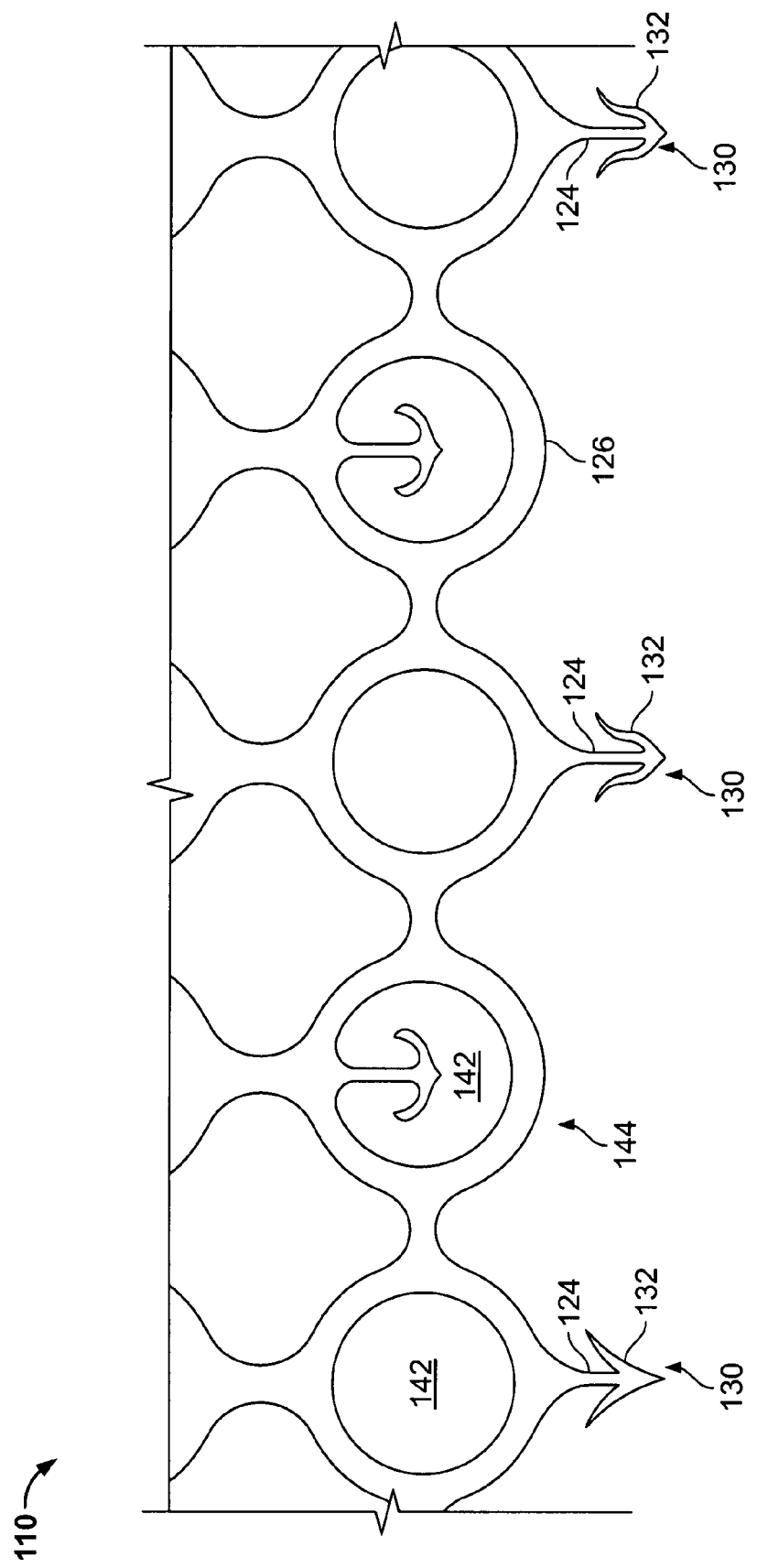
FIG. 27 is a front view of a portion of an alternative exemplary device including a plurality of cells defining a plurality of voids.
Figure 28:
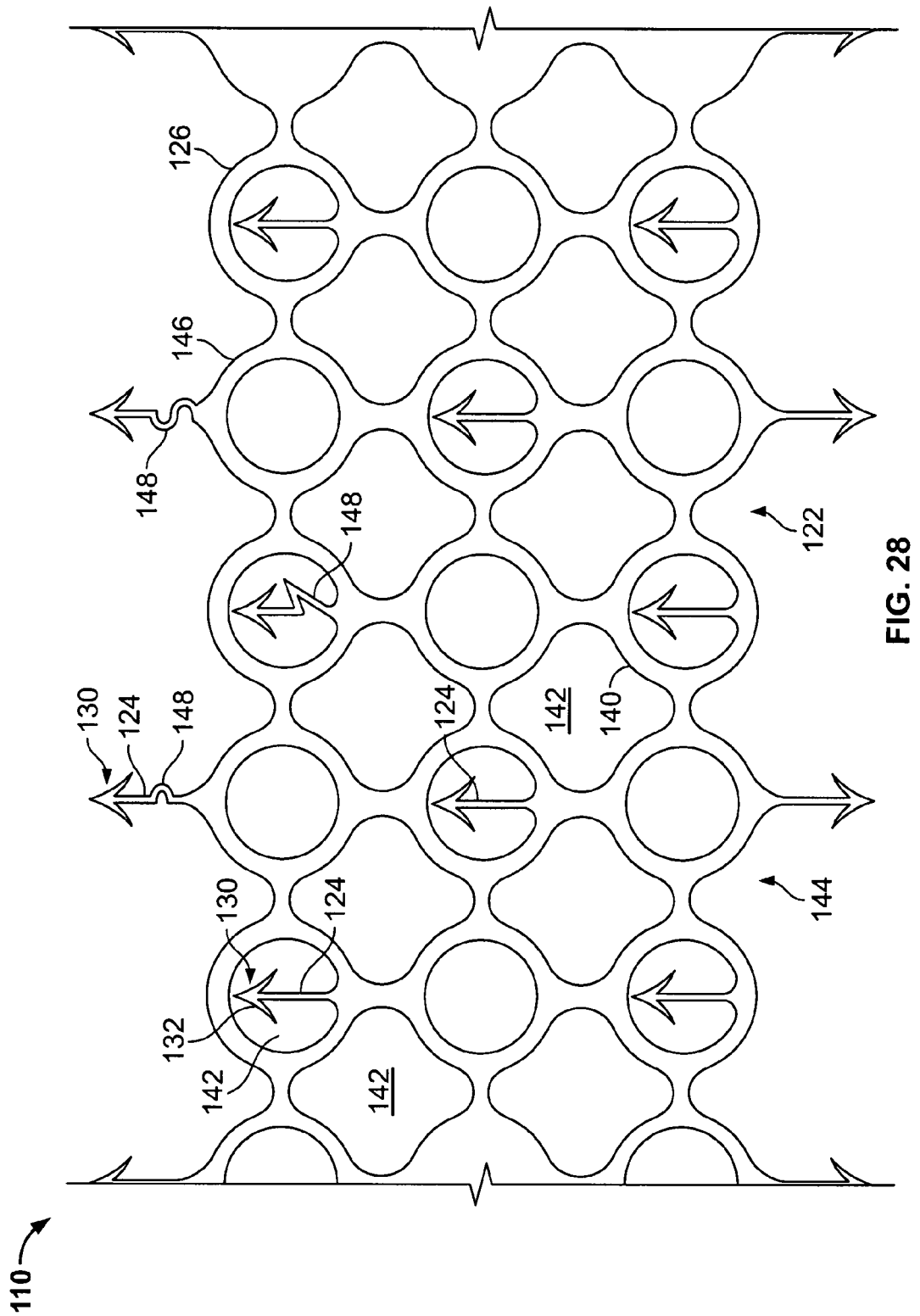
FIG. 28 is a front view of a portion of an alternative exemplary device including a plurality of cells defining a plurality of voids.
Figure 29:
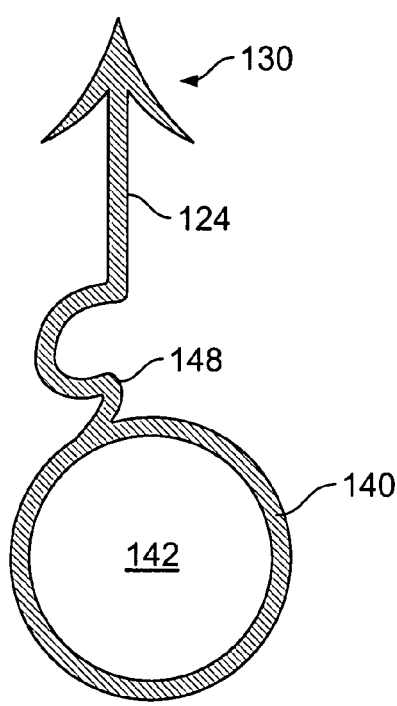
FIG. 29 is a front view of a portion of the device shown in FIG. 28 showing a cell and an exemplary retaining member having a hinge portion.
Figure 30:
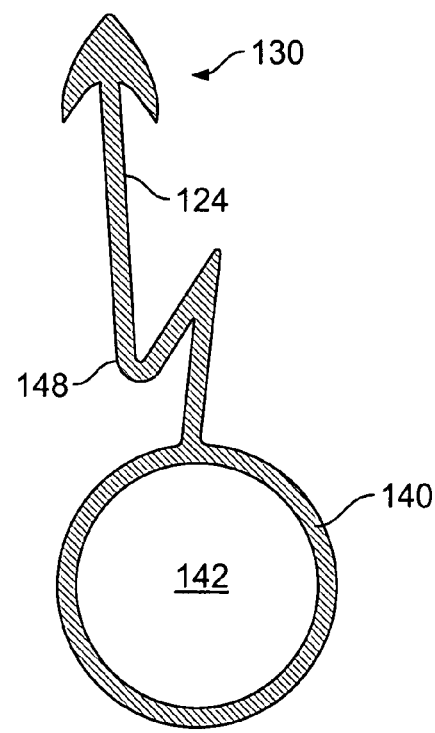
FIG. 30 is a front view of a portion of the device shown in FIG. 28 showing a cell and an alternative exemplary retaining member having a hinge portion.
Figure 31:
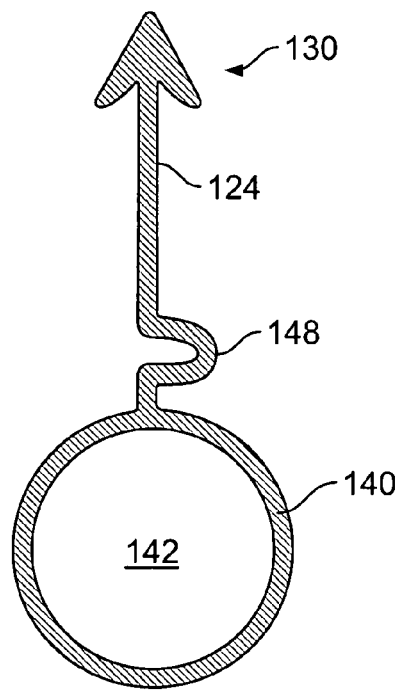
FIG. 31 is a front view of a portion of the device shown in FIG. 28 showing a cell and an alternative exemplary retaining member having a hinge portion.
Figure 32:
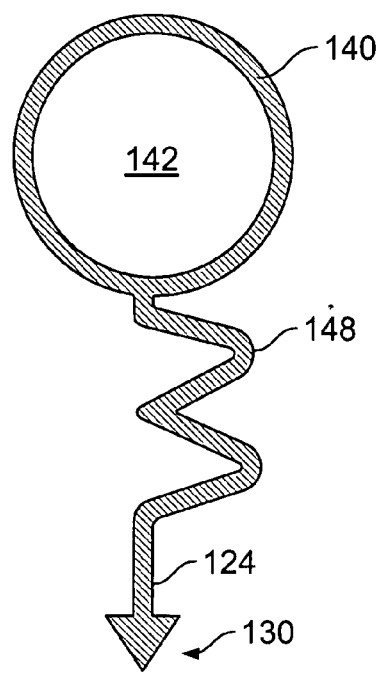
FIG. 32 is a front view of a portion of the device shown in FIG. 28 showing a cell and an alternative exemplary retaining member having a hinge portion.

In one embodiment, an implantable device 110 for gastric reduction is shown in FIG. 19. Device 110 may be used to constrict an opening formed by a stomach wall 112, such as to restrict a cross-sectional area of a cavity 114 formed by stomach wall 112 (as shown in FIG. 25). Device 110 includes a band 120 defining a cylindrical wall 122. Band 120 is made of a biocompatible material including, without limitation, suitable metal materials, such as stainless steel, platinum, gold, titanium and nickel and/or composites or alloys thereof. In the exemplary embodiment, band 120 is fabricated at least partially from a material having shape memory properties. Suitable materials include, without limitation, Nitinol and other known shape memory alloys (SMA) having properties that develop a shape memory effect (SME), which allows the material to return to an initial configuration after a force applied to the material to shape, stretch, compress and/or deform the material is removed. In a further embodiment, band 120 is fabricated from a thermally treated metal alloy (TMA) including, without limitation, nickel titanium, beta titanium, copper nickel titanium and any combination thereof. In an alternative embodiment, band 120 is fabricated at least partially from a suitable polymeric material, such as a polyurethane and/or polymethane material. It should be apparent to those having ordinary skill in the art and guided by the teachings herein provided that band 120 may be made or fabricated using any suitable biocompatible material preferably, but not necessarily, having suitable shape memory properties.

Further, band 120 may have any suitable size, shape and/or configuration, which provide sufficient structural strength as required. In one embodiment, device 110 includes at least one band 120 shaped as a tube or cylinder to define wall 122, as shown in FIG. 19, defining a general circular cross-sectional area. Alternatively, or in addition, device 110 may include at least one band 120 defining any suitable cross-sectional area, such as a polygonal cross-sectional area.

At least one retaining member 124 is formed within or coupled to wall 122. Retaining member 124 is movable between a first or retracted position substantially coplanar with an outer surface 126 of wall 122 and a second or extended position extending radially outwardly from wall 122 to facilitate coupling device 110 to stomach wall 112. In one embodiment, a plurality of retaining members 124 are formed within or coupled to wall 122. Each retaining member 124 is movable between a first or retracted position substantially coplanar with an outer surface 126 of wall 122 and a second or extended position extending radially outwardly from wall 122 to facilitate coupling device 110 to stomach wall 112. In a particular embodiment, as shown in FIG. 19, each retaining member 124 is substantially perpendicular to outer surface 126 in the extended position. In a further embodiment, each retaining member 124 is biased towards the extended position. As shown in FIG. 19, retaining member 124 includes a tip portion 130 configured to penetrate at least an inner surface 131 of stomach wall 112. In one embodiment, tip portion 130 is configured to extend through stomach wall 112 and attach to and/or interfere with an outer surface of stomach wall 112 to facilitate coupling device 110 to stomach wall 112. In one embodiment, tip portion 130 includes at least one fixed hook 132 that is configured to pass through at least inner surface 131 of stomach wall 112. Referring further to FIGS. 20-28, tip portion 130 includes any suitable number of fixed hooks 132 and/or shapeable hooks 134 (such as shown in FIGS. 33-35) having any suitable size, shape and/or configuration.

Figure 24:
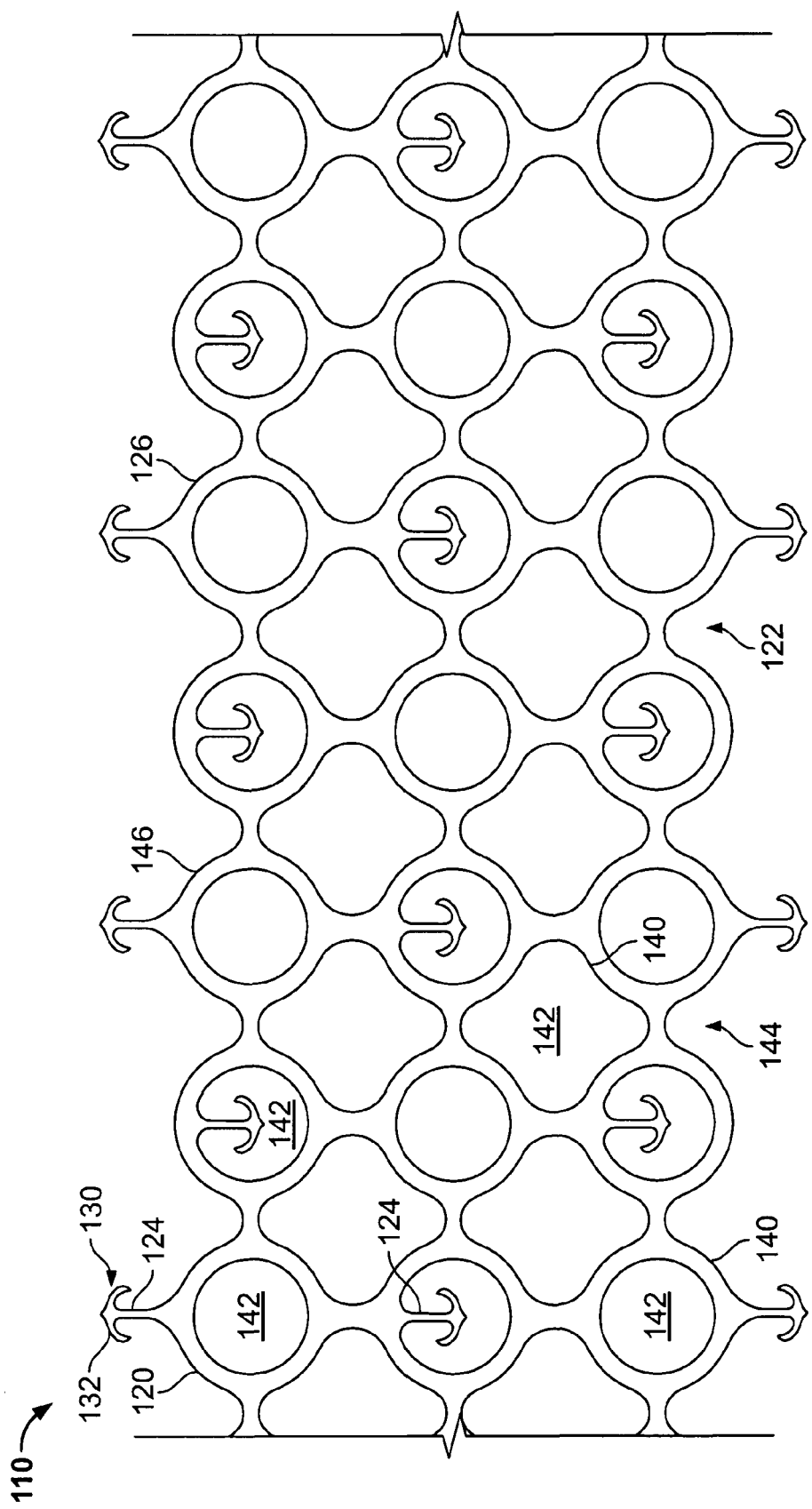
FIG. 24 is a front view of a portion of an alternative exemplary device including a plurality of cells defining a plurality of voids.

In an alternative embodiment, each retaining member 124 includes at least one needle or hook 134 that is shapeable, bendable and/or extendable. As shown in FIG. 25, each retaining member 124 includes a tip portion 130 having a plurality of extendable hooks 134 that are configured to pass through stomach wall 112 and extend to interfere with an outer surface 135 of stomach wall 112 to facilitate coupling device 110 to stomach wall 112. Referring further to FIGS. 24 and 25, in this alternative embodiment, each hook 134 is configured to penetrate through at least a portion of a thickness of stomach wall 112. Upon penetrating the thickness of stomach wall 112, each hook 134 extends radially outwardly with respect to a base portion 136 of retaining member 124 to contact and/or interfere with outer surface 135 of stomach wall 112 and secure band 120 to stomach wall 112.

Alternatively, or in addition, retaining member 124 may include a suture, staple and/or a suitable mechanical component that penetrates at least inner surface 131 of the stomach wall and extends at least partially through the stomach wall thickness to facilitate coupling device 110 to stomach wall 112.

Figure 20:
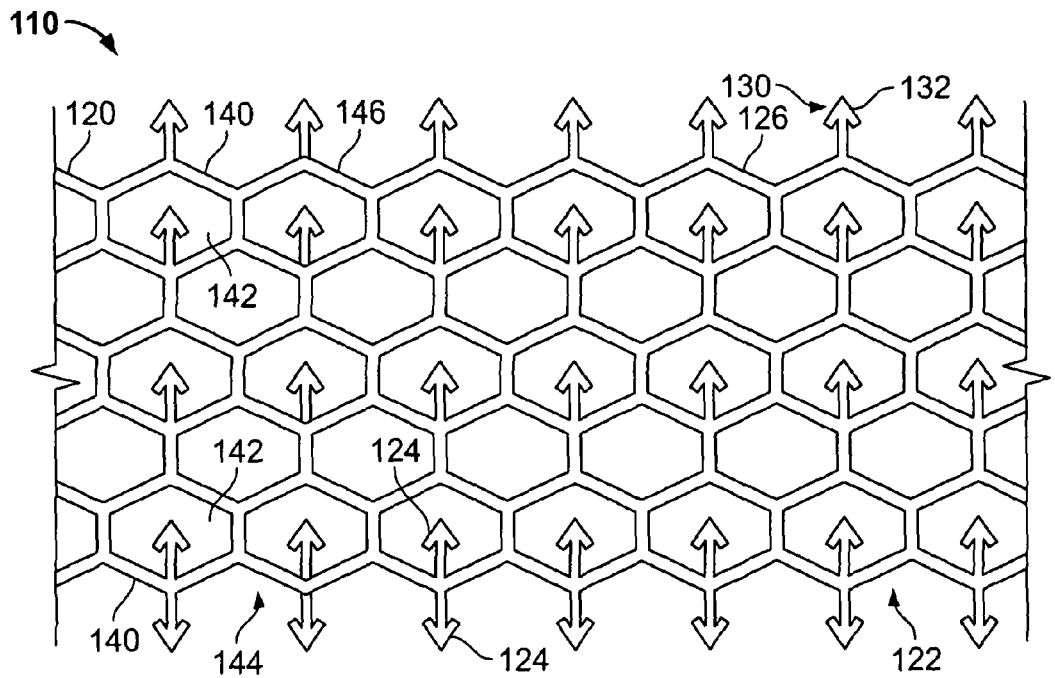
FIG. 20 is a front view of a portion of the device shown in FIG. 19 including a plurality of cells defining a plurality of voids.
Figure 21:
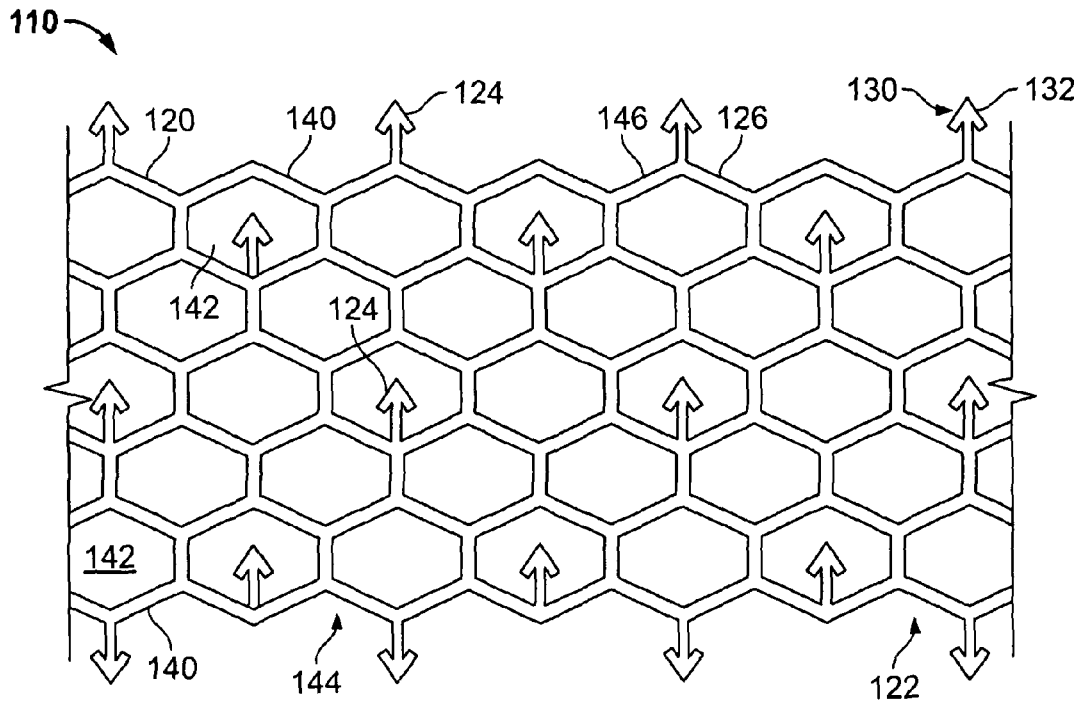
FIG. 21 is a front view of a portion of an alternative exemplary device including a plurality of cells defining a plurality of voids.
Figure 22:
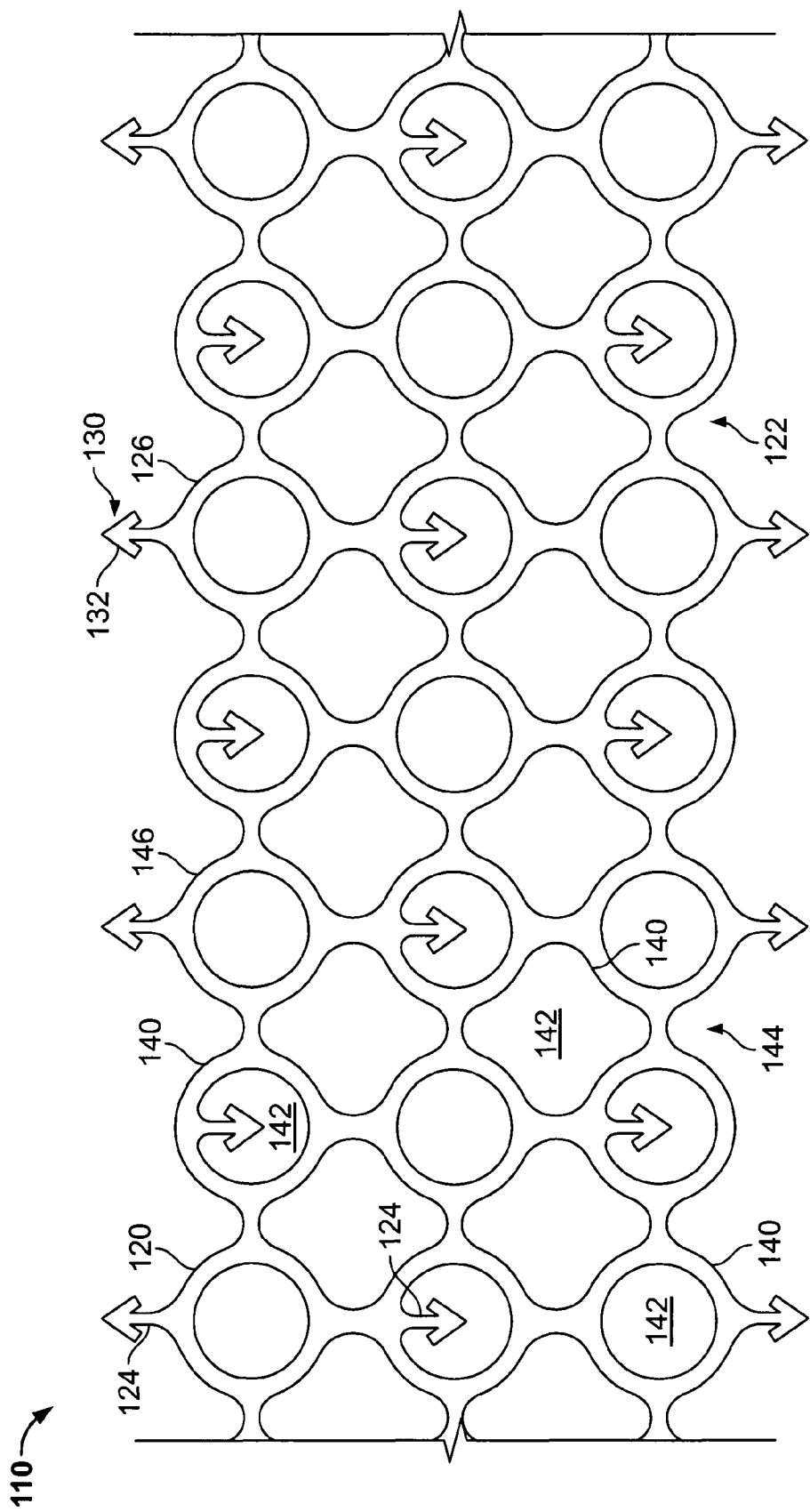
FIG. 22 is a front view of a portion of an alternative exemplary device including a plurality of cells defining a plurality of voids.
Figure 23:
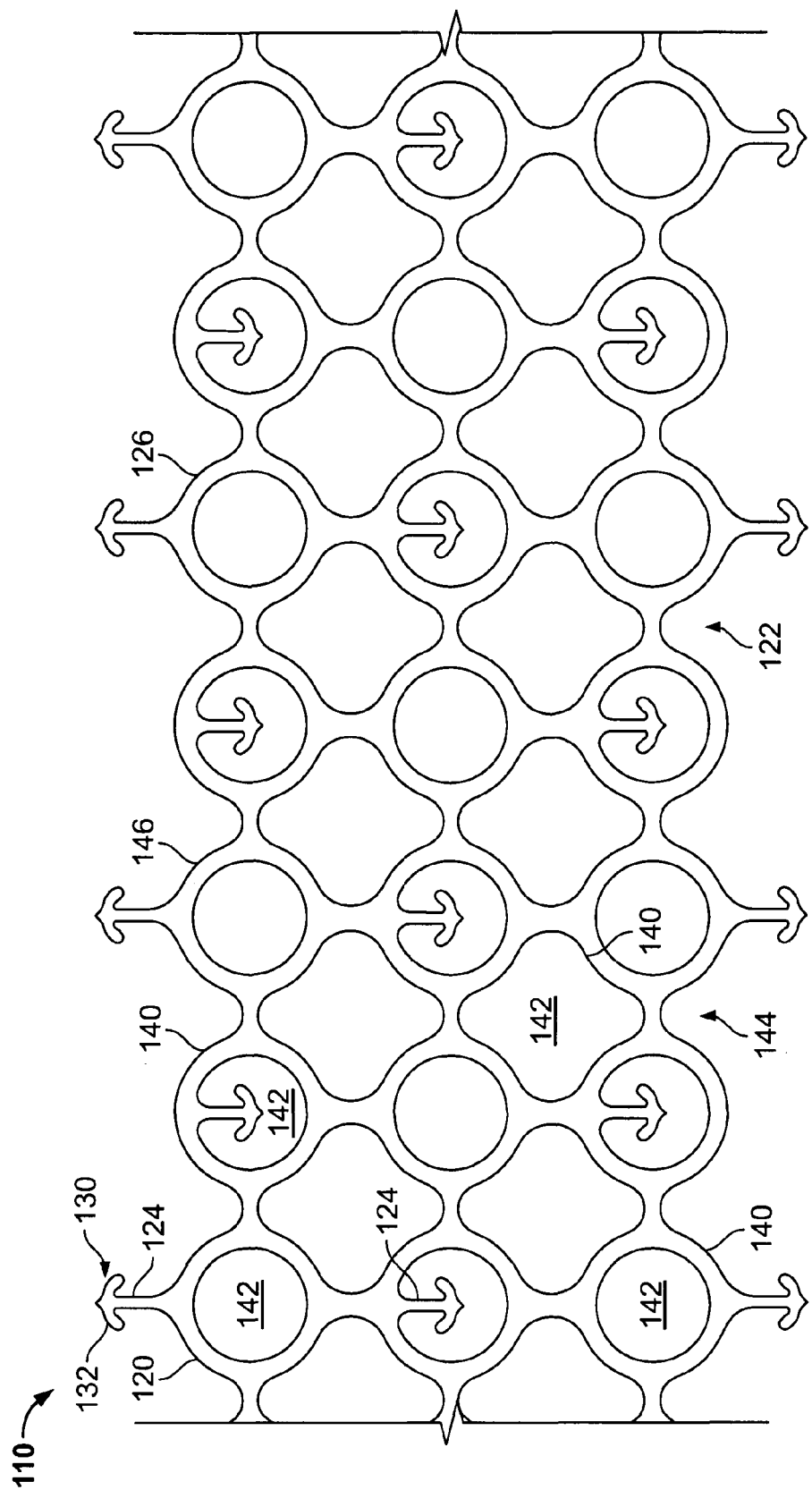
FIG. 23 is a front view of a portion of an alternative exemplary device including a plurality of cells defining a plurality of voids.

Referring further to FIGS. 20-28, in one embodiment, band 120 includes a plurality of cells 140. Each cell 140 defines a void 142 and adjacent cells 140 are coupled or integrated to form a lattice structure 144 including similar cells 140, as shown in FIGS. 20 and 21, or a lattice structure 144 including cells having a plurality of different sizes, shapes and/or configurations, as shown in FIGS. 22-28. In one embodiment, each retaining member 124 is movably coupled to or integrated with band 120. As shown in FIGS. 20-28, at least one retaining member 124 is movably coupled to a peripheral edge 146 of band 120 and/or at least one retaining member 124 is movably coupled to one cell 140 and positioned within a corresponding void 142 in the retracted position such that, in the retracted position, retaining member 124 is substantially coplanar with outer surface 126. In a particular embodiment, retaining member 124 is biased to move from the retracted position, as shown in FIGS. 20-28, to the extended positioned, wherein retaining member 124 extends radially outwardly from band 120, as shown in FIG. 19.

Referring to FIGS. 28-32, in one embodiment, retaining member 124 includes a flexible hinge portion 148 to facilitate moving retaining member 124 between the retracted position substantially planar with outer surface 126 and the extended position substantially perpendicular to outer surface 126. More specifically, as retaining member 124 moves between the retracted position and the extended position, hinge portion 148 moves to facilitate properly positioning retaining member 124 with respect to band 120. As shown in FIGS. 28-32, hinge portion may have any suitable size, shape and/or configuration that allows hinge portion 148 to move, such as twist, flex, bend, compress, extend and/or rotate, to facilitate movement of retaining member 124 with respect to band 120.

An exemplary system 150 for gastric reduction is shown in FIGS. 33-35. System 150 is used to constrict an opening formed by stomach wall 112, such as to restrict a cross-sectional area of cavity 114 formed by stomach wall 112. System 150 includes an endoscope, such as an optic fiber endoscope, and/or a catheter 152. In one embodiment, system 150 is introduced into stomach cavity 114 with the assistance or guidance of a suitable endoscope that is inserted into stomach cavity 114 through the patient's esophagus. Catheter 152 includes any suitable catheter component known to those skilled in the art and is introduced into a patient's body using any suitable or desirable method. In the exemplary embodiment, as discussed in greater detail below, catheter 152 is directed through the patient's mouth and esophagus and into an opening formed by the stomach wall. Alternatively, the catheter is introduced into the patient's stomach cavity percutaneously, i.e., by insertion through the patient's skin.

System 150 includes implantable device 110 operatively coupled to catheter 152. In one embodiment, device 110 is at least partially positioned initially about catheter 152 to facilitate introducing device 110 into the patient's body and stomach cavity. In this embodiment, a sheath 154 is movably positioned about at least a portion of band 120 to facilitate retaining retaining members 124 in the retracted position. Sheath 154 is movable with respect to band 120 to deploy retaining members 124 such that retaining members move to the extended position. In the retracted position, each retaining member 124 is substantially coplanar with outer surface 126 of wall 122. Upon introduction of device 110 into stomach cavity 114, sheath 154 is moved with respect to band 120 such that each retaining member 124 extends radially outwardly from wall 122 to facilitate coupling device 110 to stomach wall 112, as shown in FIG. 34. In a particular embodiment, each retaining member 124 is substantially perpendicular to wall 122 in the extended position. Referring to FIG. 35, in one embodiment, each retaining member 124 includes extendable hooks 134 that extend radially from base 136 of retaining member 124 and penetrate through stomach wall 112 to attach to and/or interfere with outer surface 135 of stomach wall 112.

In one embodiment, a method for restricting a cross-sectional area of a cavity formed by a stomach wall is provided. The method includes introducing into cavity 114 device 110 configured to restrict a cross-sectional area of cavity 114. Device 110 includes band 120 defining a cylindrical wall 122 and a plurality of retaining members 124 formed within wall 122. Each retaining member 124 is movable between a retracted position substantially coplanar with outer surface 126 of wall 122 and an extended position extending radially outwardly from wall 122 to facilitate coupling device 110 to stomach wall 112. With band 120 positioned about an end portion of catheter 152, sheath 154 is positioned about band 120 with retaining members 124 in the retracted position to facilitate positioning device 110 properly within cavity 114. Catheter 152 is inserted into cavity 114 through the patient's esophagus. Sheath 154 is then removed from about band 120 to allow retaining members 124 to move from the retracted position to the extended position.

In an alternative embodiment, catheter 152 defines a passage (not shown) that extends through at least a portion of catheter 152. In this alternative embodiment, device 110 is at least partially positioned initially within the passage in a retracted position and movable with respect to catheter 152 along a length of the passage to facilitate introducing device 110 into the patient's body and stomach cavity. More specifically, at least a portion of band 120 is positioned within the passage to at least partially position each retaining member 124 within the passage in the retracted position to facilitate introducing device 110 into stomach cavity 114. In the retracted position, each retaining member 124 is substantially coplanar with outer surface 126 of wall 122. Upon introduction into the stomach cavity, device 110 is extended from the passage defined by catheter 152 and positioned within cavity 114 such that in the extended position each retaining member 124 extends radially outwardly from wall 122 to facilitate coupling device 110 to stomach wall 112.

With device 110 positioned within cavity 114 as desired, in one embodiment stomach wall 112 is collapsed to urge stomach wall 112 towards device 110. Device 110 is coupled to stomach wall 112 to retain cavity 114 in a restricted configuration. In the exemplary embodiment, the cross-sectional area of the stomach cavity is restricted by applying a suction force to constrict the stomach wall. For example, a suitable suction device, such as suction device 62 described above, preferably having a plurality of apertures to provide a suitable or desired suction force, is positioned within cavity 114. Upon applying a suction force to the stomach wall, portions of the stomach wall are drawn inwardly and the cross-sectional area of stomach cavity 114 is restricted, as shown in FIG. 35. With the suction force applied, retaining members 124 penetrate stomach wall 112 and couple to stomach wall 112 to retain the stomach wall in the restricted configuration. Tip portion 130 of at least two retaining members 124 penetrate at least an inner surface of the stomach wall to couple device 110 to stomach wall 112.

In one embodiment, as shown in FIG. 35, each retaining member 124 includes a tip portion 130 having at least one flexible needle or hook 134 that punctures and penetrates stomach wall 112 to contact outer surface 135 of stomach wall 112 and maintains a secure connection thereto. In the deployed configuration, each retaining member 124 is configured to curve or bend, for example as a result of the shape memory of the material used to fabricate retaining members 124, to maintain each retaining member 124 securely coupled to stomach wall 112. Referring to FIG. 33, in one embodiment, each retaining member 124 is initially positioned within a sheath 154 that maintains flexible hooks 134 of retaining members 124 in the retracted position. After device 110 is positioned within cavity 114, sheath 154 is movable along band 120 to expose hooks 134. Each hook 134 moves to a deployed or extended position, as shown in FIG. 35, as a result of material shape memory for example, to contact outer surface 135 of stomach wall 112 and maintain a secure connection thereto.

The above-described methods and systems for gastric reduction provide a minimally invasive procedure for treating morbidly obese patients. More specifically, the above-described methods and systems facilitate restricting a cross-sectional area of a cavity formed by the stomach wall without a surgical procedure to introduce the device into the patient's stomach, as may be required by conventional procedures. As a result, treatment for morbid obesity can be reliably and efficiently administered without invasive procedures that permanently decrease the volume of the patient's stomach or bypass a portion of the stomach and/or small intestine.

Exemplary embodiments of a method and system for gastric reduction are described above in detail. The method and system are not limited to the specific embodiments described herein, but rather, steps of the method and/or components of the system may be utilized independently and separately from other steps and/or components described herein. Further, the described method steps and/or system components can also be defined in, or used in combination with, other methods and/or systems, and are not limited to practice with only the method and systems as described herein.

While the invention has been described in terms of various specific embodiments, those skilled in the art will recognize that the invention can be practiced with modification within the spirit and scope of the claims.

What is claimed is:

1. A device for restricting a cross-sectional area of a cavity formed by a stomach wall, said device comprising:
 a suction device positionable within the cavity to facilitate constricting the stomach wall towards a restricted configuration; and
 a band defining a cylindrical wall and a plurality of retaining members formed within said cylindrical wall, said band comprising a plurality of coupled cells, each of said plurality of cells defining a void, each of said plurality of retaining members substantially planar and movable between a retracted position substantially coplanar with an outer surface of said cylindrical wall and disposed within a respective void and an extended position extending radially outwardly from said cylindrical wall, wherein each said retaining member is biased towards the extended position, at least one retaining member of said retaining members comprising a base portion, a tip portion configured to penetrate at least an inner surface of the stomach wall, a barb portion configured to facilitate coupling said device to the stomach wall and retain the stomach wall in the restricted configuration, and a hinge portion configured to facilitate moving said at least one retaining member between the retracted position and the extended position, wherein said tip portion is oriented to generally point in a first direction and said barb portion is oriented to generally point in a second direction that is opposite the first direction, and said hinge portion is between said base portion and said tip portion.

2. A device in accordance with claim 1 wherein said tip portion is configured to extend through the stomach wall and couple to an outer surface of the stomach wall.

3. A device in accordance with claim 1 wherein at least one said retaining member is bendable between the retracted position and the extended position.

4. A device in accordance with claim 1 wherein each said retaining member is substantially perpendicular to said outer surface in the extended position.

5. A device in accordance with claim 1 wherein said band is fabricated at least partially from a shape memory alloy.

6. A device in accordance with claim 1 wherein said band is fabricated at least partially from a polymer material.

7. A device in accordance with claim 1 wherein each said retaining member comprises at least one of a needle, a hook, a staple and a suture.

8. A device in accordance with claim 1 wherein each said retaining member further comprises a plurality of extendable hooks, each extendable hook of said plurality of extendable hooks configured to pass through the stomach wall and interfere with an outer surface of the stomach wall.

9. A system for restricting a cross-sectional area of a cavity formed by a stomach wall, said system comprising:
a suction device positionable within the cavity to facilitate constricting the stomach wall towards a restricted configuration;
a catheter;
a device initially positioned about said catheter, said device comprising a band defining a cylindrical wall and a plurality of retaining members formed within said cylindrical wall, said band comprising a plurality of coupled cells, each of said plurality of cells defining a void, each of said plurality of retaining members substantially planar and movable between a retracted position and an extended position, in the retracted position each said retaining member substantially coplanar with an outer surface of said cylindrical wall and disposed within a respective void such that at least one of the plurality of retaining members does not extend a short distance out from the outer surface of said cylindrical wall, in the extended position each said retaining member extending radially outwardly from said cylindrical wall, wherein each said retaining member is biased towards the extended position, at least one retaining member of said retaining members comprising a base portion, a tip portion configured to penetrate at least an inner surface of the stomach wall, a barb portion configured to facilitate coupling said device to the stomach wall and retain the stomach wall in the restricted configuration, and a hinge portion configured to facilitate moving said at least one retaining member between the retracted position and the extended position wherein said tip portion is oriented to generally point in a first direction and said barb portion is oriented to generally point in a second direction that is opposite the first direction, and said hinge portion is between said base portion and said tip portion; and
a sheath movably positioned about said band to facilitate retaining each said retaining member in the retracted position.

10. A system in accordance with claim 9 wherein, in the extended position, each said retaining member substantially perpendicular to said cylindrical wall.

11. A system in accordance with claim 9 wherein said tip portion is configured to extend through the stomach wall and interfere with an outer surface of the stomach wall.

12. A system in accordance with claim 9 wherein at least one said retaining member is bendable between the retracted position and the extended position.

13. A method for restricting a cross-sectional area of a cavity formed by a stomach wall, said method comprising:
positioning a suction device within the cavity to facilitate constricting the stomach wall towards a restricted configuration;
introducing into the cavity a device configured to restrict the cross-sectional area of the cavity, the device comprising a band defining a cylindrical wall and a plurality of retaining members formed within the cylindrical wall, the band including a plurality of coupled cells, each of the plurality of cells defining a void, each of the plurality of retaining members substantially planar and movable between a retracted position substantially coplanar with an outer surface of the cylindrical wall and disposed within a void and an extended position extending radially outwardly from the cylindrical wall to facilitate coupling the device to the stomach wall, wherein each of the plurality of retaining members is biased towards the extended position, and wherein at least one retaining member of the plurality of retaining members includes a hinge portion configured to facilitate moving the at least one retaining member between the retracted position and the extended position;
collapsing the stomach wall to urge the stomach wall towards the device;
penetrating at least an inner surface of the stomach wall with a tip portion of the at least one retaining member, wherein the hinge portion is between a base portion of the at least one retaining member and the tip portion; and
coupling the device to the stomach wall to secure the cavity in the restricted configuration using a barb portion of the at least one retaining member, wherein the tip portion is oriented to generally point in a first direction, and the barb portion is oriented to generally point in a second direction that is opposite the first direction.

14. A method in accordance with claim 13 wherein introducing into the cavity a device further comprises:
positioning the device about a catheter;
positioning a sheath about at least a portion of the band with the retaining members in the retracted position;
inserting the catheter into the cavity through a patient's esophagus; and
removing the sheath from about the band to facilitate the retaining members moving from the retracted position to the extended position.

15. A method in accordance with claim 13 wherein penetrating at least an inner surface of the stomach wall further comprises penetrating at least the inner surface of the stomach wall with a tip portion of a second retaining member of the plurality of retaining members.

* * * * *